(12) United States Patent
Kokish et al.

(10) Patent No.: US 8,544,160 B2
(45) Date of Patent: Oct. 1, 2013

(54) STENT CRIMPING SYSTEM AND METHOD

(75) Inventors: Arkady Kokish, Los Gatos, CA (US);
David Lowe, Menlo Park, CA (US);
Dan Shumer, San Jose, CA (US); Scott Baron, Redwood City, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/543,591

(22) Filed: Jul. 6, 2012

(65) Prior Publication Data
US 2012/0284986 A1 Nov. 15, 2012

Related U.S. Application Data

(60) Division of application No. 12/050,031, filed on Mar. 17, 2008, now Pat. No. 8,215,149, which is a continuation of application No. 11/191,159, filed on Jul. 26, 2005, now Pat. No. 7,389,670.

(60) Provisional application No. 60/591,260, filed on Jul. 26, 2004.

(51) Int. Cl.
*B23P 11/02* (2006.01)
(52) U.S. Cl.
USPC ............................................. 29/447

(58) Field of Classification Search
USPC .................. 29/407.01, 447, 282, 283.5, 237; 72/402, 412, 416
See application file for complete search history.

(56) References Cited

U.S. PATENT DOCUMENTS

| | | | |
|---|---|---|---|
| 2,787,925 | A | 4/1957 | Buchanan |
| 3,750,453 | A | 8/1973 | Dryden et al. |
| 4,454,657 | A | 6/1984 | Yasumi |
| 5,261,263 | A | 11/1993 | Whitesell |
| 6,925,847 | B2 | 8/2005 | Motsenbocker |
| 6,931,899 | B2 | 8/2005 | Goff et al. |
| 7,021,114 | B2 | 4/2006 | Perreault |

*Primary Examiner* — John C Hong
(74) *Attorney, Agent, or Firm* — Fulwider Patton LLP

(57) ABSTRACT

A stent crimping assembly is provided for crimping a stent from a first diameter to a reduced second diameter. The crimping assembly includes a plurality of movable wedges disposed about a rotational axis to form a wedge assembly. Each wedge includes a respective first side and a second side converging to form a tip portion. The tip portions are arranged to collectively form an iris about the rotational axis thereof. The iris defines a crimp aperture about which the movable wedges are disposed. A control unit is electronically programmed to control the mechanical components. A method of calibrating the control unit includes inserting a quill of known diameter into the iris and reducing the diameter of the iris onto the quill.

11 Claims, 19 Drawing Sheets

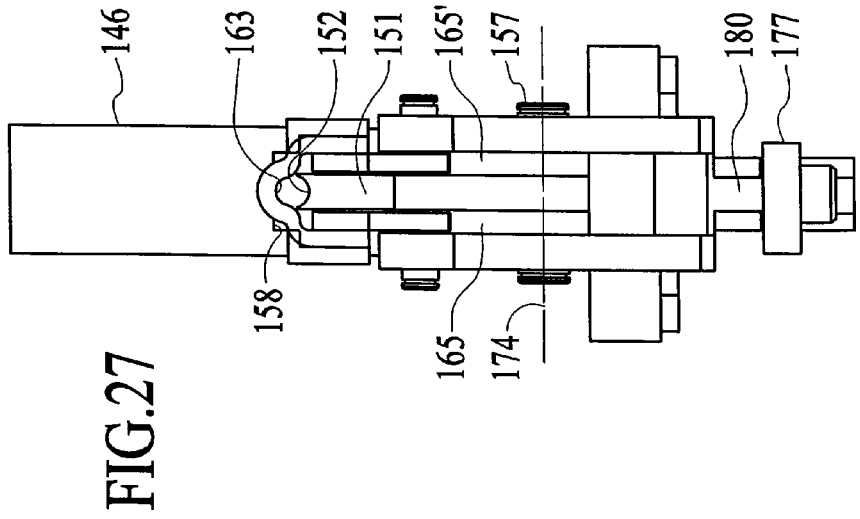
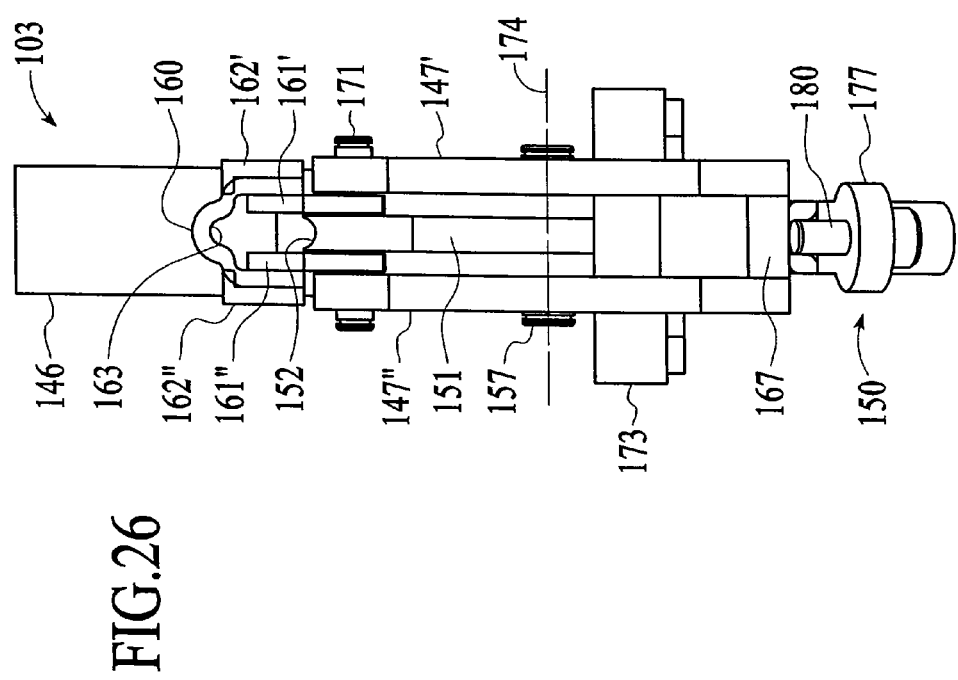

STENT CRIMPING SYSTEM AND METHOD

CROSS-REFERENCES TO RELATED APPLICATIONS

This application is a division of U.S. Ser. No. 12/050,031, filed Mar. 17, 2008, now U.S. Pat. No. 8,215,149 which is a continuation of U.S. Ser. No. 11/191,159, filed Jul. 26, 2005, now U.S. Pat. No. 7,389,670, issued Jun. 24, 2008, which claims priority to U.S. Provisional Application Ser. No. 60/591,260, filed, Jul. 26, 2004, all of which are incorporated by reference in their entirety. Applicant claims priority to all of the applications in the chain.

FIELD OF THE INVENTION

The present invention relates generally to intraluminal devices, and more particularly relates to apparatus and methods for reducing the size of these devices, such as a stent, stent-graft, graft or vena cava filter, for percutaneous translumninal delivery thereof.

BACKGROUND

A number of vascular diagnostic and interventional medical procedures are now performed translumenally. For example, catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body, through a puncture in the femoral artery for example, and into the vascular lumen. Catheters or other medical devices are advanced into the patient's vasculature through the introducer sheath, and procedures such as balloon angioplasty, stent placement, etc. are performed.

In particular, stents and stmt delivery assemblies are utilized in a number of medical procedures and situations, and as such their structure and function are well known. A stmt is a generally cylindrical prosthesis introduced via a catheter into a lumen of a body vessel in a configuration having a generally reduced diameter for transport and delivery, and then expanded to a diameter of the target vessel when deployed. In its expanded configuration, the stent supports and reinforces the vessel walls while maintaining the vessel in an open, unobstructed condition.

Balloon expandable stents are well known and widely available in a variety of designs and configurations. Balloon expandable stents are crimped to their reduced diameter about the delivery catheter, then maneuvered to the deployment site and expanded to the vessel diameter by fluid inflation of a balloon positioned between the stent and the delivery catheter. One example of a stent is described in US patent application having Publication No. 2004/0093073, published May 13, 2004, the content of which is incorporated herein by reference.

During advancement of the stem, through a body vessel to a deployment site, the crimped stent must capable of securely maintaining its axial position on the delivery catheter. That is, the crimped stent must not translocate proximally or distally during advancement, and especially must not dislodge from the catheter. Stents that are not properly crimped, secured or retained to the delivery catheter may slip and will either be lost, be deployed in the wrong location or only be partially deployed. Moreover, the stent must be crimped in such a way as to minimize or prevent distortion of the stent, and thereby, minimize or prevent abrasion and/or trauma to the vessel walls. Additionally, if a stent has been coated with a beneficial agent, care must be taken when crimping the stent onto the delivery device that the coating is not disturbed or removed from the stent during the crimping process.

In the past, crimping has been performed by hand, often resulting in an undesirable application of uneven radial crimping forces to the stent. Such a stent must either be discarded or re-crimped. Stents that have been crimped multiple times can suffer from fatigue and may be scored or otherwise marked which can cause thrombosis. In fact, a poorly crimped stent can also damage the underlying balloon.

In addition to hand crimping of stents, automated crimping machines have been developed, wherein the automated crimping machines provide a more consistent crimp radial force during the crimping process or consistent profile. In addition to providing consistent crimping forces, many other crimping parameters can be closely controlled through the use of computer controls or mechanical controls. An example of such an automated crimping machine and related crimping methods can be seen in U.S. Pat. No. 6,629,350 to Motsenbocker. The crimping machine shown and described in the '350 patent includes a crimp head comprising a plurality of segments, wherein one end of each of the segments is constrained to rotate about a pin wherein the other end of the segments is allowed to translate about a second pin. In this arrangement, the translation of the second end of each of the segments controls the size of the opening formed by the distal ends of the segments. A shortcoming of such a design is wear of each of the segments at the pins. The increased wear increases the tolerances through which the crimp head can be operated, eventually the crimp head can no longer be held to a desired tolerance and therefore must be rebuilt. Thus there is a need for an improved crimp head design that can be held to tighter tolerances for a significant period of operation.

In addition to the balloon expandable stents described above, it would be desirable to provide a stent crimping system capable of loading (i.e., crimping) selfexpanding stents into a delivery device, wherein the stent can be chilled during compression. Further still, once compressed into a delivery diameter, the crimped stent must then be inserted into a distal end of a delivery system while maintaining the delivery profile. In order to accomplish this, the crimping head must be constructed such that minimal friction exists between the stent and the head. Additionally, the delivery device must be retained relative to the crimping head and then advanced a known distance to insert the crimped stent, without damaging the delivery device.

SUMMARY OF THE INVENTION

The present invention provides an apparatus and methods for mechanically crimping a generally tubular stent from a first diameter to a second diameter. A stent crimping assembly is provided that includes a plurality of movable wedges having respective first side and a second side converging to form a tip portion. The tip portions are arranged to collectively form an iris about a rotational axis thereof. The iris defines a crimp aperture about which the movable wedges are disposed. Each wedge is associated with a stationary structure and a rotational actuation unit such that during rotation of the actuation unit about the rotational axis, the iris is caused to rotate about the rotational axis, relative the stationary structure, for inward movement of the wedges to decrease the size of the crimp aperture and outward movement of the wedges to increase the size of the crimp aperture.

Accordingly, during the crimping procedure, the stent is also caused to rotate with the iris. When released, the partially or fully crimped stent will remain at least partially rotated relative to the initial position before a crimp. This is advantageous for any subsequently repeat crimp. Often, in a conventional crimping process, the crimp should be repeated several times in order to achieve a smaller profile and better and more uniform circularity. Each time, between operations, the stent or crimper should be rotated relative to each other to achieve this result. In the present invention, this rotational procedure automatically becomes part of the process, and hence the manual process of rotating the stent or crimper during the repeat crimp procedure can be eliminated.

In one specific embodiment, the movable wedges have at least one end section coupled to the stationary structure for relative rotational displacement therebetween, and another section of the movable wedge coupled to the actuation unit for substantially relative linear displacement therebetween. The rotational coupling of each wedge to the stationary structure is positioned proximate to a distal portion of the respective wedge, and the linear coupling of each wedge to the actuation unit is positioned proximate to a proximal portion of the respective wedge.

A further specific arrangement, the relative rotation displacement of each wedge is about a respective rotational axis that extends substantially parallel to the rotational axis of the iris. The relative linear displacement of each wedge is in a direction that extends substantially perpendicular to a respective bisecting plane of each wedge. The rotational coupling of each wedge to the stationary structure further includes a respective linear displacement along a respective bisecting plane of each wedge for movement toward the aperture during the inward movement thereof, and movement away from the aperture during the outward movement thereof.

Another embodiment includes the stationary structure with a stationary end wall that includes a plurality of bearing devices disposed about the rotational axis of the iris. Each bearing device is associated with one respective wedge, and each wedge end section defining the elongated slot extending in a direction along the respective centerline of the wedge.

In yet another specific embodiment, the actuation unit includes a housing enclosing the plurality of movable wedges. The housing rotatably couples the stationary end wall for rotational displacement about the rotational axis of the iris. A respective slider mechanism couples a respective wedge to the housing for the respective substantially linear displacement of the respective proximal portion of the wedge to the housing during the rotational displacement of the housing. The slider mechanism includes a linear bearing device mounted to the wedge, and a carriage unit slideably coupled to the bearing device for movement in a direction substantially perpendicular to respective bisector of the wedge.

In another aspect of the present invention, a stmt crimper system includes an iris composed of a plurality of movable wedges disposed about an aperture. The iris includes a rotational axis about which the wedges rotate as a unit. The wedges are disposed between substantially concentric first end walls and an actuation housing substantially centered about the rotational axis and rotatably coupled to the first end walls. Each wedge is associated with the first end walls and the actuation housing such that during rotational movement of the actuation housing, the iris is caused to rotate about the rotational axis, relative a stationary structure, for inward movement of the wedges to decrease the size of the aperture and outward movement of the wedges to increase the size of the aperture.

In one specific embodiment, the first end walls are stationary end walls affixed relative to the stationary structure. In another arrangement, the actuation housing includes a pair of opposed rotational end walls rotatably coupled to a respective first end wall. Each of the rotational end walls and the first end walls are configured for rotational displacement, relative one another, about the rotational axis.

In still another aspect of the present invention, a crimping apparatus is disclosed for reducing the diameter of a medical device. The apparatus includes at least one end plate; at least one drive plate; and a crimping assembly. The crimping assembly includes a plurality of blades, wherein the blades have a proximal and distal end and a tapered portion adjacent the distal end. A pivot member is disposed on each side of each blade, and the pivot member is configured to be received by the drive plate. The blades further include a sliding assembly, a portion of the sliding assembly coupled to the blade adjacent the proximal end and a second portion of the sliding assembly coupled to the end plate.

In yet another aspect of the present invention, a stmt crimping system is provided including a chassis, a crimping assembly, a clamping assembly and a control unit. The clamp assembly that secures the medical device includes a lower clamp device defining a seating groove formed and dimensioned to seat a portion of the medical device therein. A retaining assembly includes an elastomeric member, the elastomeric member defining a contacting groove oriented in an opposed manner proximate to at least a portion of the seating groove. An actuation mechanism is associated with the retaining assembly and the lower clamp device such that operation thereof causes the retaining assembly to move between an opened condition, enabling positioning of the elongated device between the lower clamp device and the retaining assembly, and a closed condition, retaining the medical device between the contacting groove of the elastomeric member and the seating groove of the lower clamp device.

In another specific embodiment, the clamp device includes a pivot lever rotatably mounted to the lower clamp device. The pivot lever cooperates between the actuation mechanism and the retaining assembly for movement of the retaining assembly between the opened condition and the closed condition.

The retaining assembly is coupled to the pivot lever proximal a distal portion of the lever member. Further, the actuation mechanism cooperates with the pivot lever proximal a proximal portion thereof such that when the actuation mechanism is moved from a first position towards a second position, the pivot lever is caused to rotated about a rotational axis of the pivot pin which causes the retaining assembly to move from the opened condition toward the closed condition.

In yet another specific embodiment, the lower clamp device includes a base portion and a support plate extends distally from the base portion. The seating groove extends along an upper edge portion thereof from the base portion to the support plate. The retaining assembly includes a pair of plate members mounted to, and depending downwardly, from the elastomeric member on opposite sides of the support plate. Each plate member is coupled to the pivot lever at the distal portion thereof.

The pivot lever includes a pair of lever portions disposed on opposite sides of the lower clamp device support plate. E lever portion is pivotally mounted to a corresponding plate member through a securing pin extending therethrough. The support plate includes an elongated slot upon which the securing pin passes therethrough. The elongated slot be configured to accommodate the travel of the securing pin as the retaining assembly reciprocates between the opened condition and the closed condition.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 26 is a front elevation view of the clamping assembly of FIG. 19, illustrated in the opened condition.

FIG. 27 is a front elevation view of the clamping assembly of FIG. 26 illustrated in the closed condition.

DETAILED DESCRIPTION OF THE PREFERRED EMBODIMENTS

Figure 1:
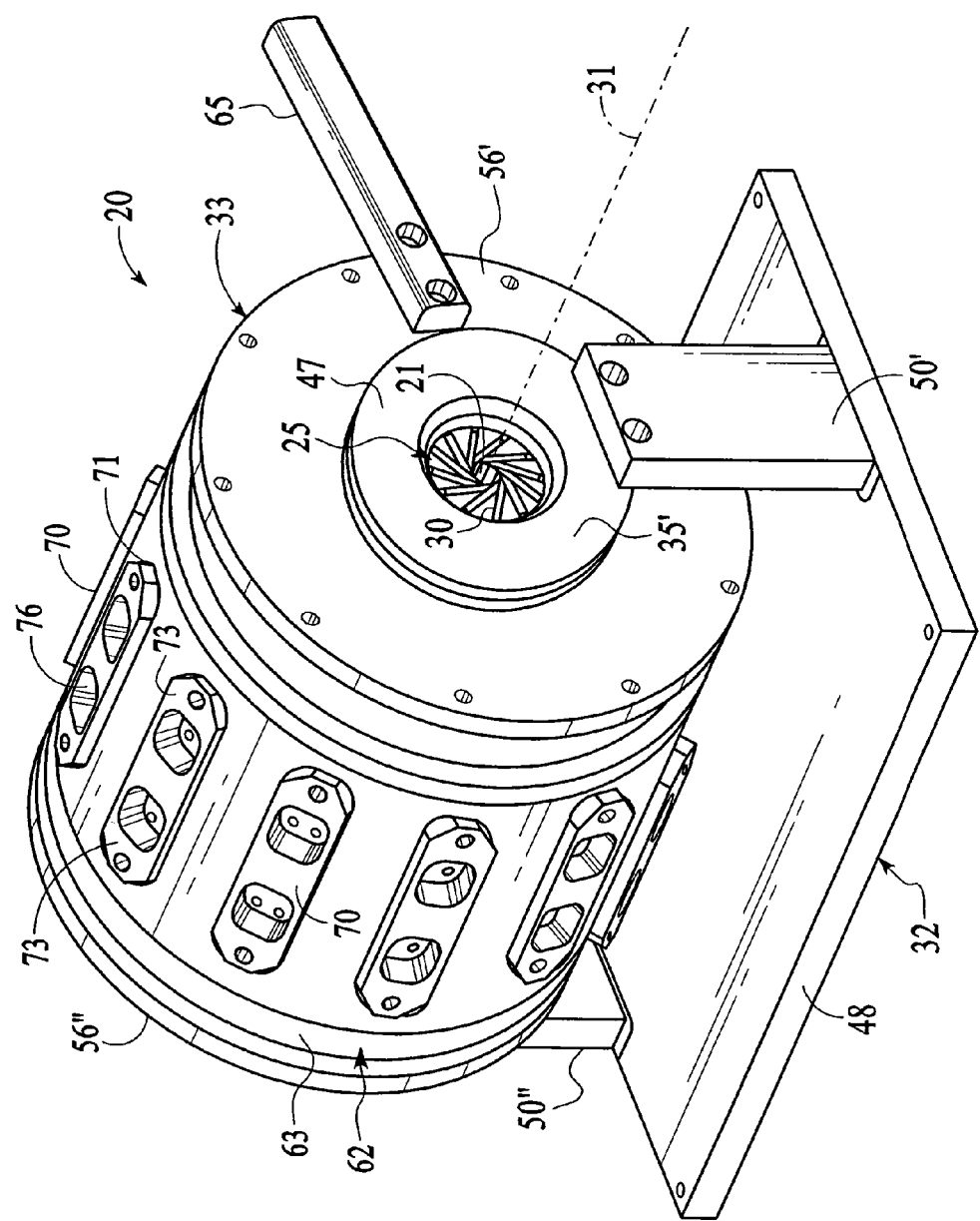
FIG. 1 is a top perspective view of a crimping assembly constructed in accordance with the present invention, and illustrating a crimp aperture in an opened condition.
Figure 2:
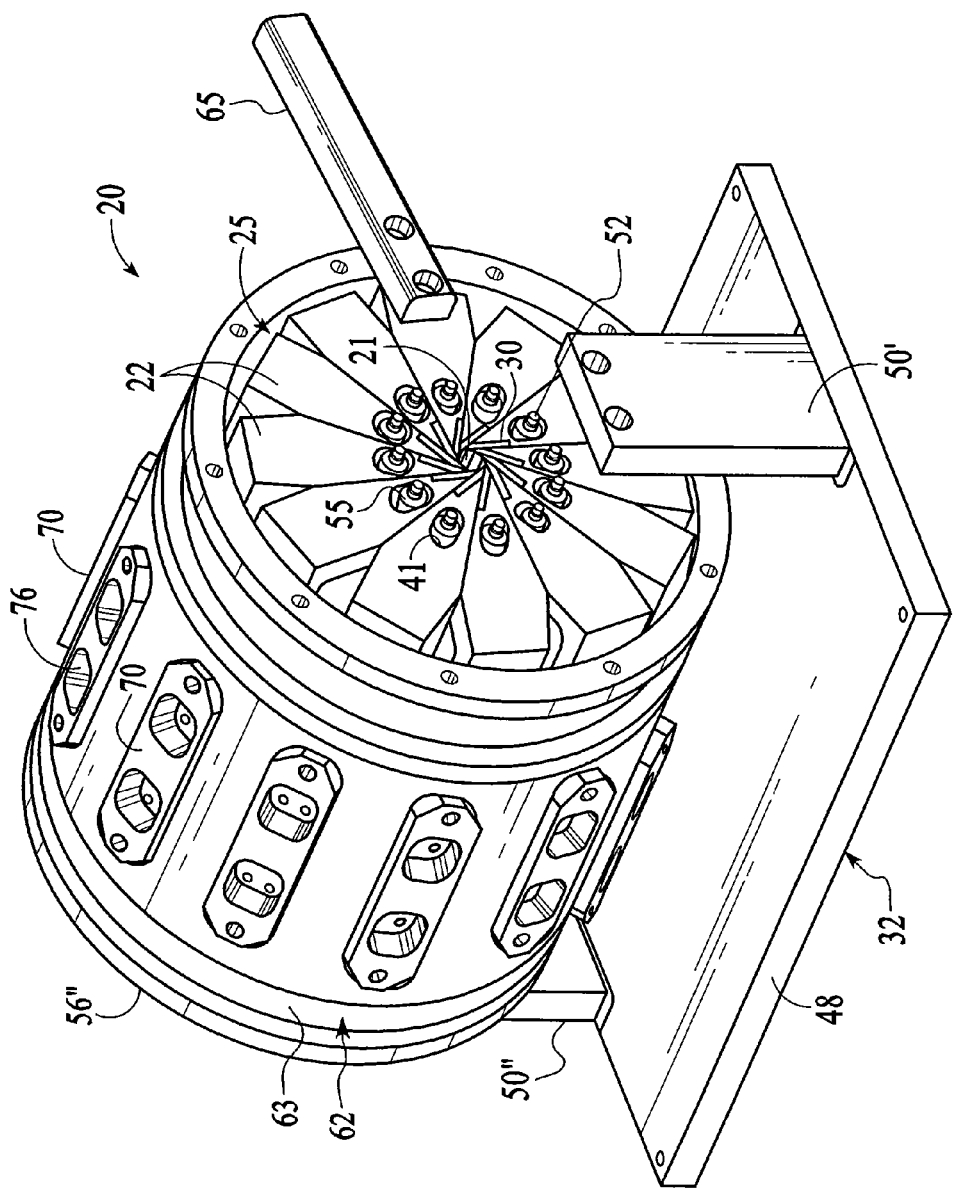
FIG. 2 is a top perspective view of the crimping assembly of FIG. 1 with a proximal rotational end wall and a proximal stationary end wall removed.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 3:
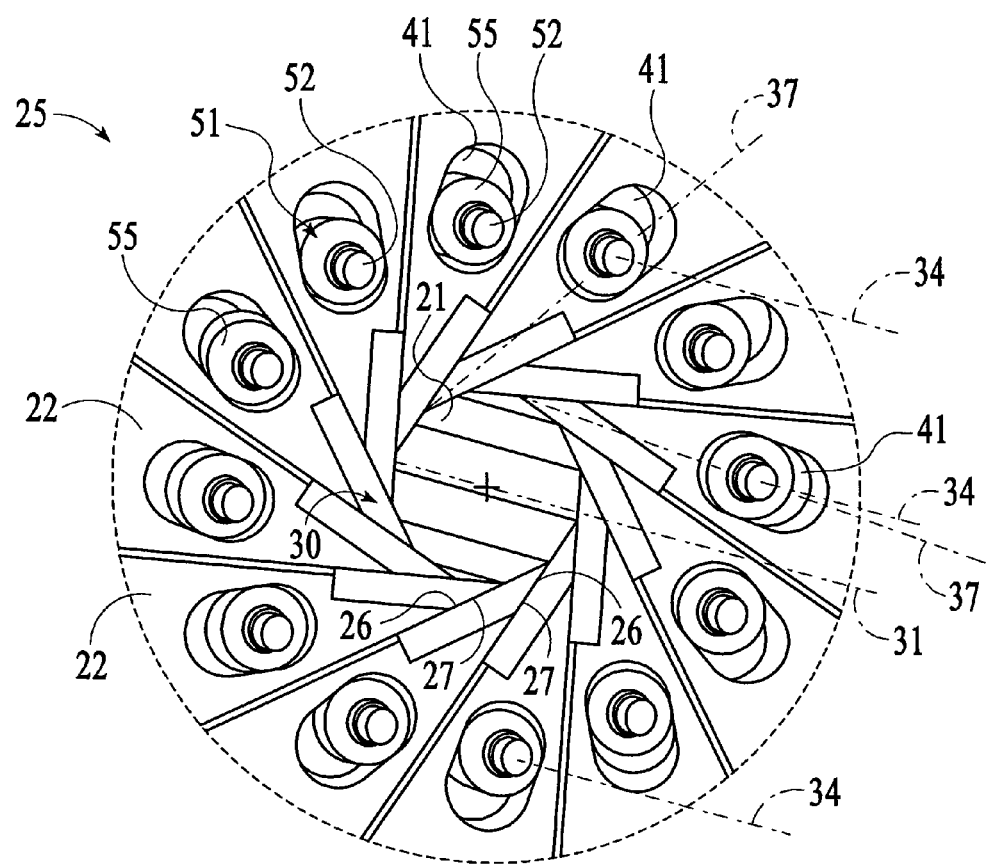
FIG. 3 is an enlarged, fragmentary, top perspective view of the iris of the crimping assembly of FIG. 2.
Figure 4:
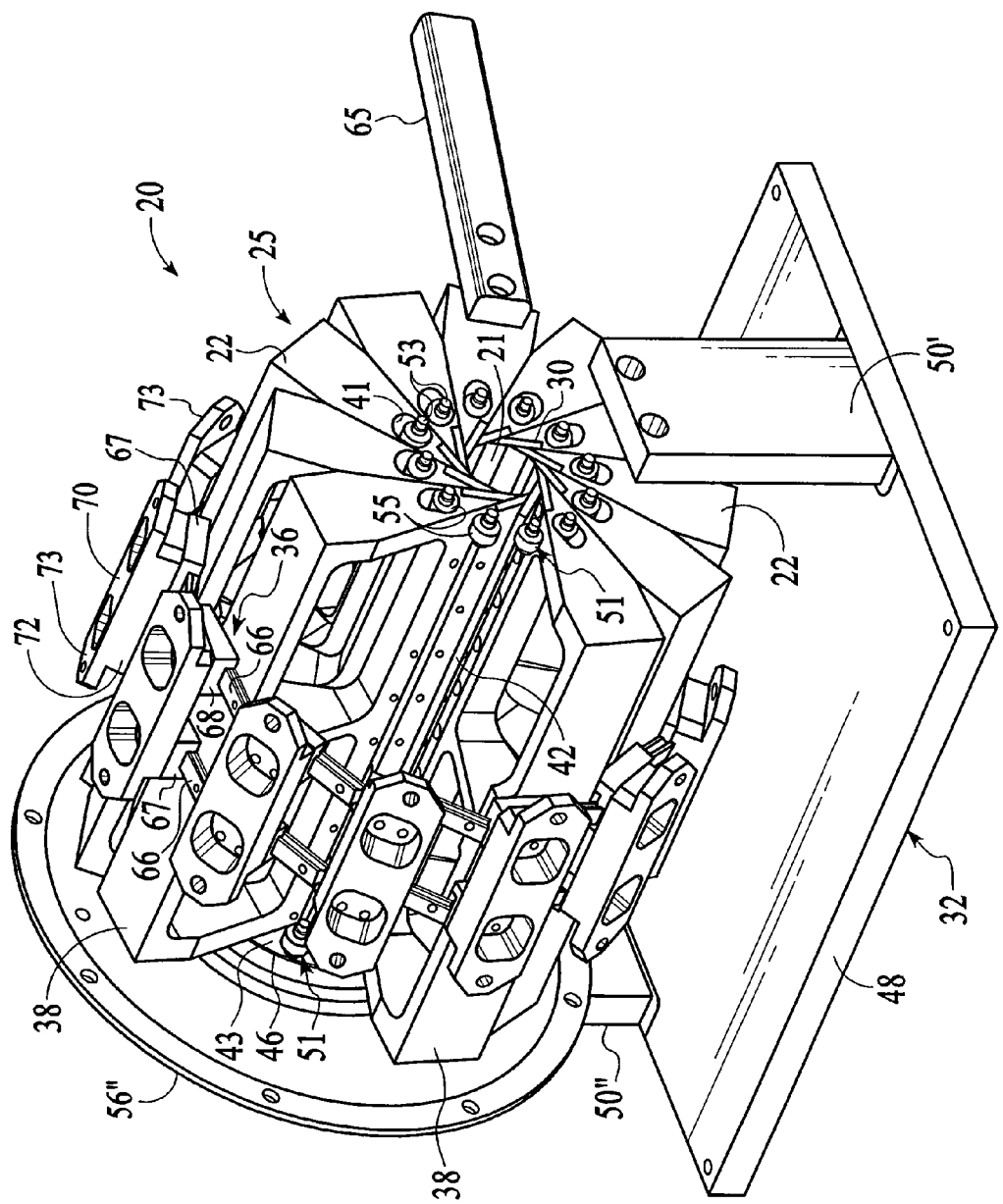
FIG. 4 is a top perspective view of the crimping assembly of FIG. 2 with the drum portion removed.
Figure 5:
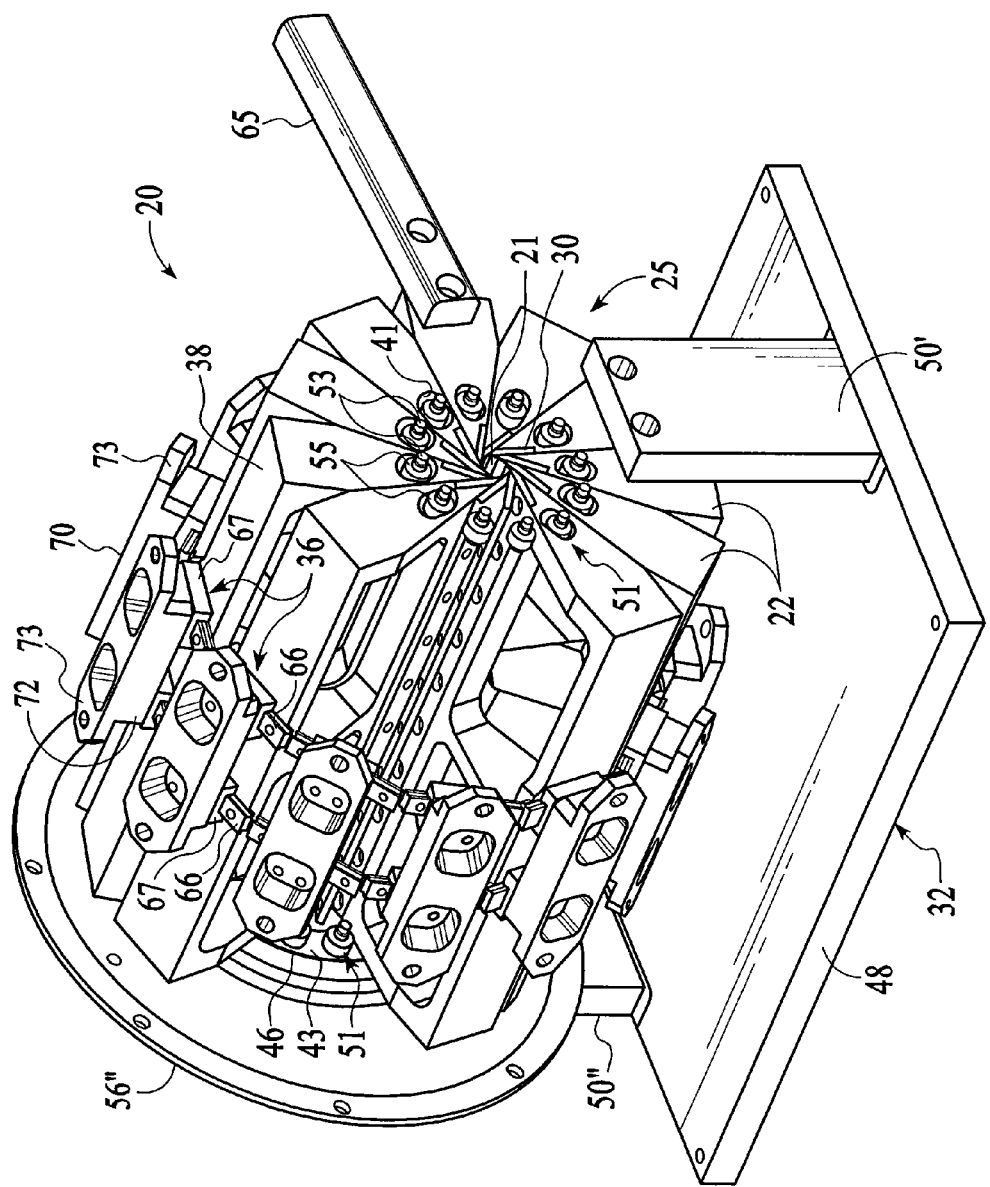
FIG. 5 is a top perspective view of the crimping assembly of FIG. 4, illustrating the crimp aperture in a closed condition.

Referring now to FIGS. 1-6, a stent crimping assembly, generally designated 20, is illustrated that defines a crimp aperture 21 for crimping a stent (not shown) from a first diameter (FIG. 4) to a reduced second diameter (FIG. 5). This crimping assembly 20 includes a plurality of movable blades or wedges 22 arranged in an assembly 25 around the crimp aperture 21. Each wedge, as best viewed in FIGS. 3 and 6, include a first side 26 and a second side 27 that converge to form a distal tip portion 28. When assembled in the wedge assembly 25, the first and second sides 26, 27 of each wedge 22 are arranged substantially adjacent the second and first sides 27, 26, respectively, of an adjacent wedge 22 such that the tip portions 28 collectively form an iris 30. The iris 30 defines the crimp aperture 21 centered about the iris rotational axis 31. Hence, the distal portions of the wedges 22 are directed generally inwardly while the proximal portions of the wedges are directed generally outwardly.

As will be described in greater detail below, the crimping assembly 20 includes a stationary structure 32 and a rotational actuation unit 33 that is rotatably associated with the stationary structure for rotation of the unit about the iris rotational axis 31. Each movable wedge 22 of the wedge assembly 25 is rotationally coupled to the stationary structure 32 proximate to a respective distal portion thereof such that each wedge 22 can rotate about a respective wedge rotational axis 34 thereof. Collectively, the wedge rotational axes 34 are radially spaced about the iris rotational axis 31 (FIG. 3). Each wedge rotational axis is oriented substantially parallel to, and circumferentially spaced-apart about, the iris rotational axis 31. Further, a proximal portion of each wedge 22 is coupled to the actuation unit 33 through respective linear slider mechanisms 36 for substantially linear displacement relative to its coupling to the actuation unit. More particularly, as will be described the linear displacement is in a direction substantially perpendicular to a respective centerline or plane 37 bisecting the wedge 22.

Figure 8:
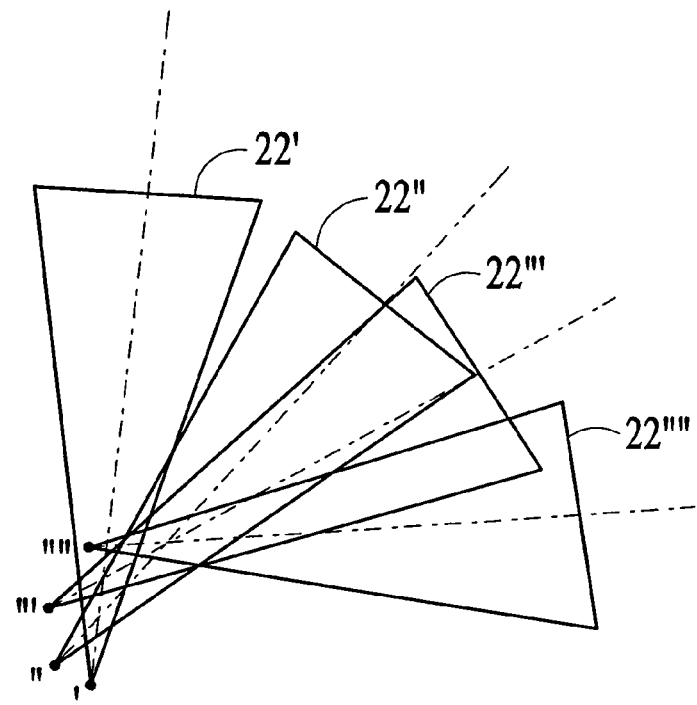
FIG. 8 is a diagram illustrating the trajectory of a single wedge during operation, in four positions.
Figure 9:
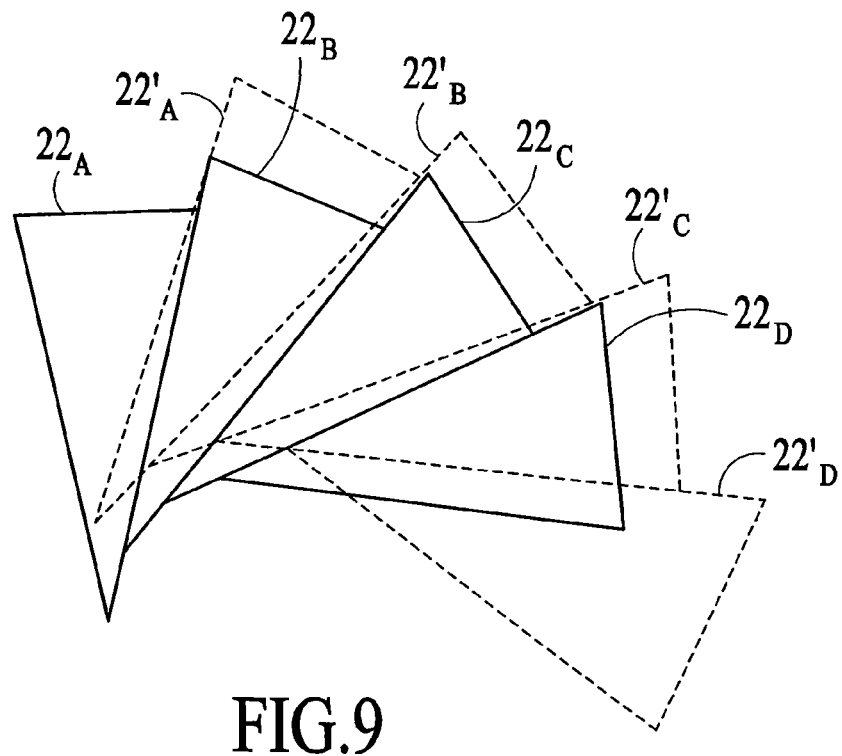
FIG. 9 is a diagram illustrating the relative movement of four adjacent wedges during operation, in two positions.

In accordance with the present invention, since the linear slider mechanisms 36 are collectively caused to rotate with the actuation unit 33 about the iris rotational axis 31, each wedge 22 is caused to rotate about its wedge rotational axis 34, while simultaneously sliding linearly (via the respective slider mechanism) relative to the rotating actuation unit 33. Hence, the motion of the each wedge 22 relative a first end wall 35', 35" and the stationary structure 32 (as well as to the wedge rotational axis 34 which is fixed relative to the stationary structure) is represented in the single wedge trajectory diagram of FIG. 8 and the relative movement of the multiple wedges of FIG. 9. Collectively, the iris 30 itself is caused to rotate as a unit about the iris rotational axis 31, relative to the stationary structure 32. This is advantageous in that the stent is also caused to rotate. When released, the partially or fully crimped stent will remain at least partially rotated relative to the initial position before a crimp. Often, in a conventional crimping process, the crimp should be repeated several times in order to achieve a smaller profile and better and more uniform circularity. Each time, the stent or crimper should be rotated between these operations relative to each other to achieve this result. In the present invention, this rotational procedure automatically becomes part of the process, and hence the manual process of rotating the stmt or crimper during the repeat crimp procedure can be eliminated.

Accordingly, in operation, when the actuation unit 33 is rotated about the iris rotation axis, in a counter-clockwise direction shown in FIGS. 1, 4 to the position of FIG. 5 (which illustrates the crimping assembly 20 with most of the actuation unit removed), the counter-clockwise motion is translated into both rotational movement of each respective wedge about its wedge rotational axis 34, while further simultaneously displacing each wedge linearly inward along the respective slider mechanism. The linear displacement, for each slider mechanism 36, is in a direction substantially perpendicular to a respective plane bisecting the each wedge 22. As the entire iris 30 rotates relative to the stationary structure 32, the inward sliding movement of the wedges 22 causes the aperture 21 to decrease in size. As the crimp aperture 21 closes (FIG. 5), a radially inward force, as well as a counter clockwise rotational force, is applied by the blades to the medical device (e.g., a stent) disposed in the aperture.

The actuation unit is rotated until the desired size reduction of the aperture and medical device is achieved. Subsequently, the actuation unit 33 is rotated in the oppose direction to permit removal of the device from the crimp aperture.

Figure 6:
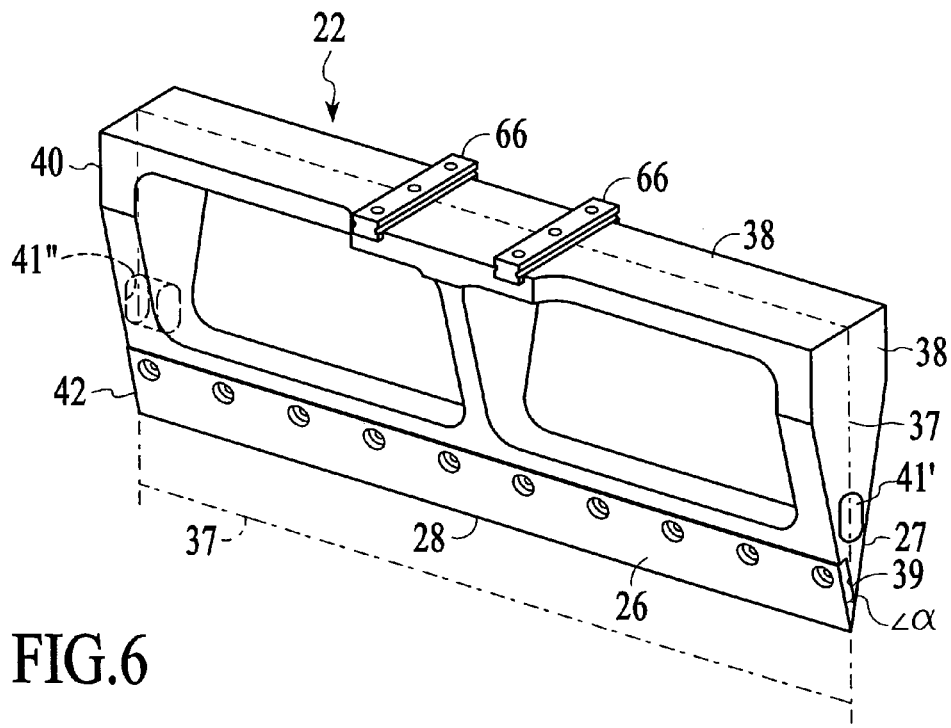
FIG. 6 is an enlarged top perspective view of a single wedge device of the crimping assembly of FIG. 1.
Figure 7:
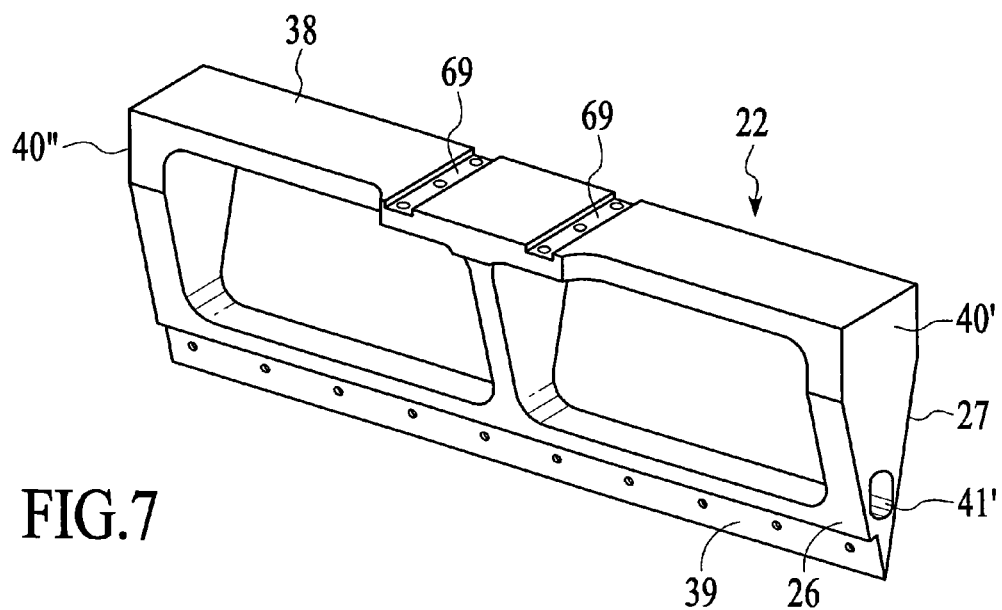
FIG. 7 is a reduced top perspective view of the frame structure of the wedge device of the FIG. 6.

Turning now to FIGS. 6 and 7, a blade or wedge 22 of the crimping assembly is shown and illustrated as having a wedge shape that is generally symmetrical about the respective centerline or bisecting plane 37 thereof. In this specific embodiment, the wedge 22 includes an elongated hollow frame structure having an inwardly tapered distal end and a widened proximal portion with a substantially planar proximal end 38. Preferably, the aforementioned first side 26 and the opposed second side 27 are substantially planar, and taper inwardly to form a straight tip portion (thus forming a substantially polygonal crimp aperture 21). The distal end of the first side 26, however, may be slightly curved toward crimp aperture 21 (not shown), so as to form a more circular-shaped aperture when the crimp aperture is fully closed or reduced in size. Further, the tip portion may also terminate at a sharp edge. Preferably, however, the edge is slightly rounded or beveled, eliminating a sharp tip. This configuration facilitates sliding contact with the adjacent blade surfaces. Briefly, while the present invention has been shown and described as providing sliding, abutting contact between the wedge side walls, it will be appreciated that there may be some clearance therebetween with no sliding contact.

Depending upon the number of blades selected to form the iris 30, the converging angle between the first side 26 and the second side 27 (i.e., the tip angle a) can be selected accordingly. For example, the wedge assembly may include as little as three wedges, and as many as sixteen. The maximum number of wedges is limited by the number thereof that can be physically coupled together under the relevant size constraints. As the number of blades is increased, the profile of the aperture and of thus of the crimped medical device becomes smoother. In the embodiment illustrated in FIGS. 1-5, twelve wedges 22 are employed where the first side 26 and the second side 27 of each blade are in substantially adjacent one another, or in sliding contact with the second side 27 and the first side 26, respectively, of the adjacent blades. Generally the tip angle a is less than or equal to 360/n where n is equal to the number of blades. For the twelve-blade embodiment illustrated, the tip angle a is in the range of about 30 Degrees or less.

As best illustrated in FIG. 6, each wedge 22 is further defined by a substantially planar first end section 40' and an opposed substantially planar second end section 40". Each face of the end section defines an elongated bearing slot (41', 41") extending substantially in a direction along the centerline 37 that bisects each wedge. Each bearing slot of the set (41', 41") is further aligned relative to one another, and is positioned proximate to the distal portion of the wedge 22.

The wedges 22 may be constructed of a material or a combination of materials such as nylon, delrin, steel, aluminum, titanium, TEFLON®, plastics, composite materials, and other suitable materials. This hollow framing of the wedge 22 also may be constructed of multiple pieces that may be assembled to form a unitary member, or alternatively each wedge 22 may be constructed as a unitary member. In another specific embodiment, each wedge 22 may include a replaceable blade insert 42 at each distal end thereof. At a distal portion of each wedge 22, the first side 26 thereof defines a step or shoulder portion 39 formed to seat the elongated blade insert 42 therein (FIG. 7). In this arrangement, one side of the blade insert 42 seats substantially flush with the first side 26 of the wedge, while an opposed side of the blade insert seats substantially flush with the second side 27. Accordingly, the entire contacting surface that is employed to crimp a stent may be provided by these replaceable blade inserts 42. Such blade inserts 42, by way of example, may also be composed of nylon, delrin, TEFLON®, plastics, composite materials, and other suitable materials. Such material selections depend in part upon the material properties, such as the thermo insulation, the thermo conductivity, whether the friction therebetween is low or high, etc.

In accordance with one embodiment of the present invention, the first end walls 35', 35" are substantially stationary, and are part of and mounted to stationary structure 32. These stationary end walls (i.e., a proximal end wall 35' and a distal end wall 35") are disposed at opposite ends of the wedge assembly 25. Preferably, these stationary end walls 35', 35" each include an exterior surface and an opposed interior face 43 that is to be oriented to face inwardly toward the wedge assembly when assembled. A receiving port 45 extends therethrough from the exterior to the interior face 43 to that provides access to the crimp aperture 21. Each end wall 35', 35" includes a respective hub portion 46 that is oriented to face inwardly, toward the wedge assembly 25, during operation and assembly of the crimping assembly 20. The stationary end walls 35', 35" each further include a mounting flange 47 that extends radially outward from the hub portion 46.

Figure 10:
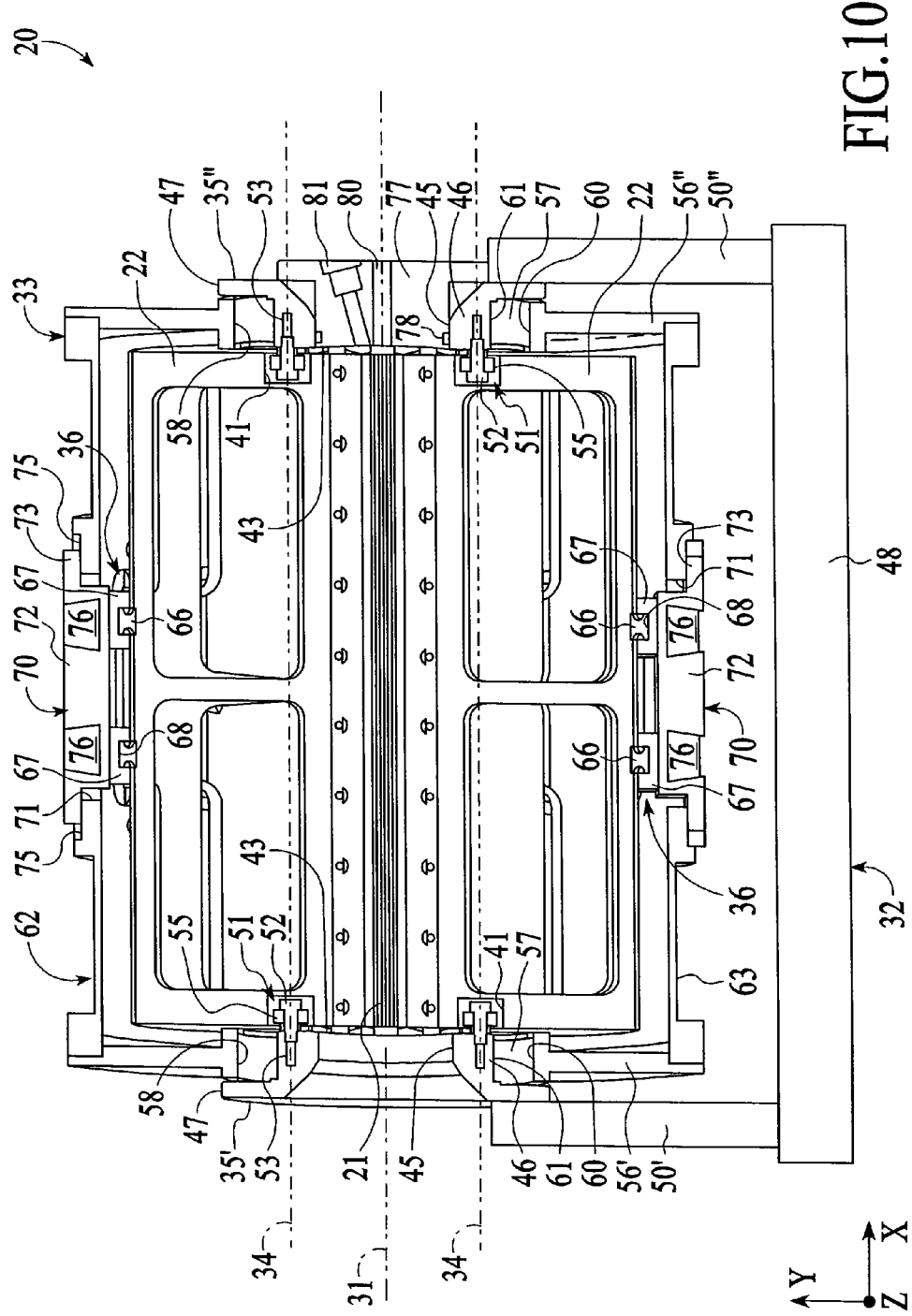
FIG. 10 is a side elevation view, in cross-section, of the crimping assembly of FIG. 1.

FIGS. 1 and 10 best illustrate that the stationary structure 32 further includes a support base 48 and a pair vertical supports 50', 50" upstanding therefrom. Each vertical support 50', 50" is substantially rigidly mounted to the respective end wall mounting flange 47 to secure the end walls 35', 35" in a stationary manner. It will be appreciated, of course, that the stationary end walls may be rigidly supported through any other conventional technique as well.

To rotatably support the assembly 25 of wedges 22 to the stationary structure 32, each wedge 22 is rotatably coupled, at the opposed end sections 40', 40" thereof, to the corresponding stationary end wall 35', 35" for rotation about a respective wedge rotational axis 34. As best illustrated in FIGS. 2-5 and 10, such rotational support is provided by a plurality aligned bearing devices 51 disposed at the opposed end sections 40', 40" of each wedge 22. Each respective pair of bearing devices 51 cooperate to define the respective wedge rotational axis 34 about which each wedges individually rotates. To mount the wedge assembly 25, the bearing device pairs are affixed to the interior face 43 of the hub portions 46 of the stationary end walls 35', 35" and configured rotatably cooperate with, and support, the respective wedges 22.

Briefly, each bearing device 51 includes a pivot shaft 52 having a pin end 53 suitable for affixed mounting into the interior face 43 of the respective hub portion 46 (FIGS. 4, 5 and 10). These pin ends 53 may be friction fit, threaded or adhered to the interior face 43 in any secure manner. The pivot shaft 52 on the interior face 43 of the proximal stationary end wall 35' is to be co-axially aligned with the pivot shaft 52 on the interior face 43 of the distal stationary end wall 35" so that the respective wedge rotational axis 34 is substantially parallel to the iris rotational axis 31.

Rotatably mounted to each pivot shaft 52 is a corresponding wheel 55 (flange) rotatably supported about the shaft through ball bearings or the like. These wheel flanges 55 and pivot shafts 52 of the bearing devices are configured for receipt in the corresponding bearing slots 41', 41" defined by the first and second end sections 40', 40" of the respective wedge.

As illustrated, each bearing device 51 is aligned with its corresponding bearing on an opposite end of the wedge assembly. Collectively, these bearing pairs are equally spaced apart radially about the iris rotational axis, thus also positioning the wedge rotational axes 34 equally spaced apart radially about the iris rotational axis. Moreover, these radially spaced wedge rotational axes 34 are oriented substantially parallel to the iris rotational axis 31, which center the rotation of the iris 30 about the iris rotational axis 31. Accordingly, during operational movement, the respective wedge rotational axes 34 of the wedge assembly 25 remain stationary relative the stationary end walls 35', 35", while each respective wedge 22 simultaneously rotates about its wedge rotational axis, and slides substantially linearly a direction substantially perpendicular to the respective centerline 37 of the respective wedge 22.

In order to permit such linear sliding displacement in the aforementioned direction, each wedge 22 themselves must also be capable of sliding linearly along the respective bearing devices in a direction along the centerline plane. The bearing slots 41', 41", each of which extend in a direction along the centerline plane, accommodate this motion.

Therefore, these bearing couplings not only promote relative rotation of the wedges 22 about the respective wedge rotational axis 34, via the wheel flanges 55, but also promote linear displacement along the respective bearing slot 41', 41" generally toward and away from the iris rotational axis. The width of the bearing slot, therefore, is sufficiently larger than the diameter of the corresponding wheel flange 55 to permit such sliding linear displacement along the elongated bearing slot as well as to promote rotation of the respective wedge 22 about the respective wedge rotational axis 34. The tolerance between the slot width and the wheel (flange) diameter, however, must also be sufficiently small to reduce and minimize instability and chatter during operation.

In contrast, the length of the elongated bearing slots 41', 41" must be sufficient to permit the relative linear displacement of wheel flange 55 along the slot. This linear displacement essentially translates into movement of the rotating wedges 22 respectively toward and away from the crimp aperture 21.

While the present invention has been illustrated and described as having the bearing slots defined by the end sections 40', 40" of the wedges 22, and the bearing devices 51 mounted directly to the hub portions 46 of the stationary end walls 35', 35", it will be appreciated such mounting componentry can be easily reversed. In such a configuration, therefore, the bearing devices 51 can be mounted to the wedge end sections 40', 40", while the bearing slots will be defined by the interior wall of the hub portion 46. In this arrangement, however, respective the bearing slots 41', 41" will not be substantially linear, and will shaped to substantially mirror the path of the wedge and wedges shown in the diagrams of FIGS. 8 and 9.

Referring back to FIG. 1, a rotational actuation unit 33 is rotatably mounted to the stationary structure 32 to actuate the rotation of the wedge assembly 25 about the iris rotational axis 31, and to cause the increase or decrease of the diameter of the iris 30. Briefly, as above-mentioned, the actuation unit 33 is rotatably coupled to the stationary end walls 35', 35" for rotation the iris rotational axis 31, while simultaneously individually coupled to the proximal portions of the respective wedges 22 for substantially linear displacement therebetween.

In one specific embodiment, the actuation unit 33 is provided by a housing structure that at least partially encloses the cylindrical wedge assembly 25 therein. FIGS. 1 and 10 best illustrate that the rotational actuation unit 33 includes a pair of rotational end walls (i.e., a proximal rotational end wall 56' and the distal rotational end wall 56") that rotatably cooperate with the corresponding stationary end walls 35', 35", respectively, for rotational support. These rotational end walls 56', 56" are disposed on the opposed ends of the wedge assembly 25, and are rotatably coupled to the hub portions 46 of the stationary end walls 35', 35" through respective rotational bearings 57.

Hence, each plate-like rotational end wall 56', 56" defines a central bearing aperture 58 that is centered about the iris rotational axis, when rotatably supported to the respective hub portion 46. This bearing aperture 58 is defined by an inward facing mounting surface 60 of the rotational end walls 56', 56" that, when centered, opposes an outward facing mounting surface 61 of the respective stationary end wall 35', 35". As shown in FIG. 10, the rotational bearing 57, such as for example a conventional ball bearing assembly, is disposed between these mounting surfaces 60, 61 to provide rotational support of the respective rotational end walls 56', 56" about the corresponding stationary end walls 35', 35". These bearing units 57, hence, provide the primary rotational support of the actuation unit 33 about the iris rotation axis.

It will be appreciated, however, that such a ball bearing unit can be eliminated and a more direct bearing-style contact could be employed between the inward facing mounting surface 60 of the rotational end walls 56', 56" and the outward facing mounting surface 61 of the respective stationary end wall 35', 35".

Further, it will be contemplated that the first end walls 35', 35" (i.e., the stationary end walls when affixed to the stationary structure 32) may also rotatably coupled to the stationary structure for rotation about the aperture rotational axis. In this instance, both the rotational end walls 56', 56" may be mounted to rotational support structure to enable relative rotation therebetween, and relative to the stationary structure 32, wherein the cross-support structure 62 (FIG. 11) would be supported by a rotatable member such as bearings (not shown). In this embodiment, the end walls 35', 35", 56' and 56" would be configured to move either independent of each other or in conjunction with each other, the cross-support structure 62 being rotationally coupled to the stationary structure 32.

Figure 16:
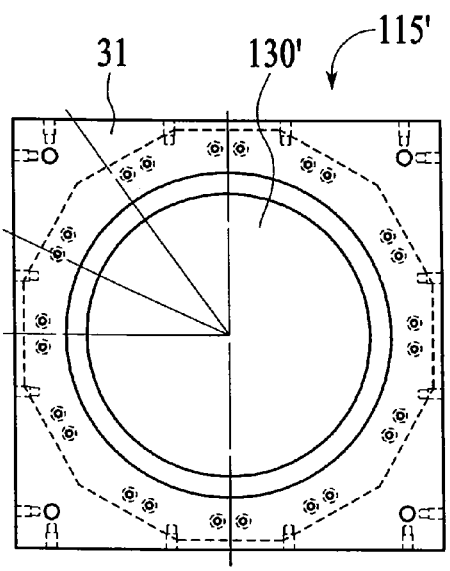
FIG. 16, is a rear elevation view of the end plate of FIG. 15.

To rigidify the actuation units, so as to operate as a single unit, a cross-support structure 62 laterally extends from the proximal rotational end wall 56' to the distal rotational end wall 56". Generally, in one specific arrangement, this support structure 62 may be provided by a plurality of cross-beams that extend laterally across the wedge assembly 25. FIG. 16 best illustrates such a configuration where the cross-beams 140 extend across the wedge assembly, and are spaced-apart circumferentially about the aperture.

Figure 11:
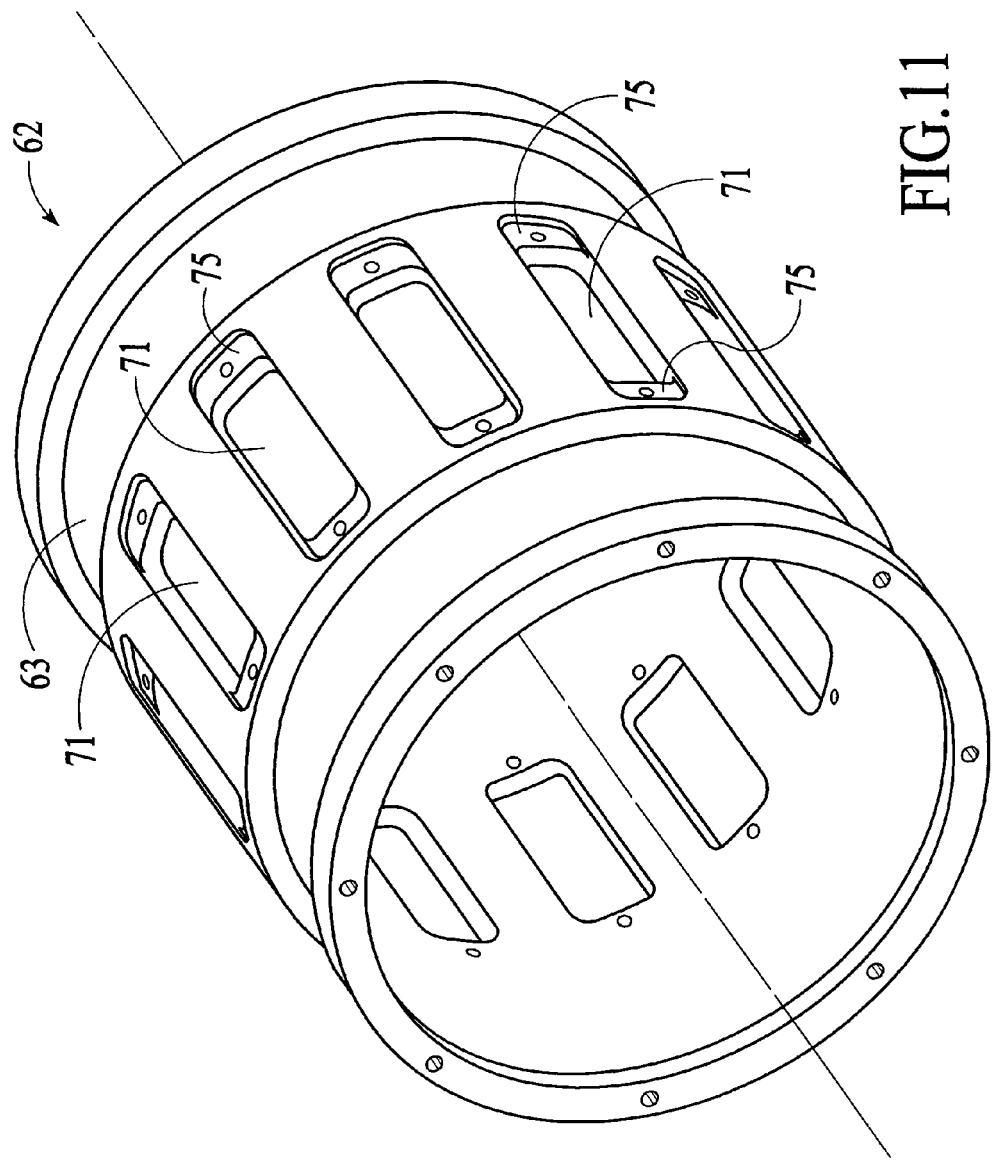
FIG. 11 is top perspective view of a drum portion of an actuation unit of the clamping assembly of FIG. 1.

In the preferred embodiment of this specific arrangement, however, the cross-support structure 62 is provided by a unitary cylindrical-shaped drum portion 63 (FIG. 11). As shown in FIGS. 1 and 10, this unitary drum rigidly mounts the proximal rotational end wall 56' to the distal rotational end wall 56", together as a unit. This cylindrical-shaped housing structure is sized and dimensioned to essentially fully enclose the entire wedge assembly 25 therein without impeding movement of the wedges during rotational movement of the actuation unit 33.

A handle member 65 can be mounted to the actuation unit 33 for rotational actuation of the unit about the iris rotational axis 31. As illustrated in FIG. 1, a single handle member 65 can be mounted to the proximal rotational end wall 56' for manual rotation thereof. It will be appreciated, however, that such handle member can be mounted to either or both rotational end walls 56', 56", as well as to the drum portion 63. Moreover, as will be described in greater detail below, conventional automated controls can be incorporated as well to automate the actuation movement.

In accordance with the present invention, a proximal portion of each wedge 22 is slideably coupled to the actuation unit 33, via the slider mechanisms 36, to promote substantially linear displacement of the wedge relative to the actuation unit. Each slider mechanism 36 is preferably disposed between the actuation unit 33 and the proximal portion of the respective wedge, in a manner permitting substantially linear sliding displacement in a relative direction, substantially perpendicular to the respective centerline or bisecting plane 37 of the respective wedge 22. As mentioned above, this simultaneous, respective linear wedge displacement occurs as the entire wedge assembly 25 is rotating about the iris rotational axis 31 as a unit, and as the wedges further rotate about their respective wedge rotational axis 34.

In one specific embodiment, the slider mechanisms 36 include a pair of spaced-apart substantially linear bearings 66 mounted to the respective wedge 22, and a pair of corresponding carriage units 67 coupled to the actuation unit 33. These carriage units 67 are configured to track linearly along the associated linear bearing 66. In particular, as best viewed in FIG. 7, the two rails or linear bearing 66 are seated and affixed in a pair of corresponding alignment grooves 69 recessed the surface of the substantially planar proximal end 38 of each respective wedge 22. These alignment grooves 69 orient the respective linear bearing 66 so that the corresponding carriage units 67, in sliding contact therewith, will slide a substantially linear direction substantially perpendicular to the respective centerline of the wedge.

The carriage units 67 are generally U-shaped having a substantially planar outer surface, and a receiving slot 68 on an opposed surface that faces inwardly toward the respective wedge 22. These receiving slots 68 are formed and dimensioned of sliding receipt of the corresponding linear bearing 66 therein for linear displacement of the carriage emit 67 therealong.

While the application of the pair of spaced-apart linear bearings 66 is preferred for stability and alignment, it will be appreciated that a single linear bearing or more than two bearing can be employed without departing from the true nature and scope of the present invention.

The crimping assembly 20 further includes a plurality of saddle units that fixedly mount each pair of carriage units 67 to the actuation unit 33. Each saddle unit 70 is configured to seat in a corresponding access port 71 extending through the drum portion 63. These access ports 71 are equally spaced circumferentially about the drum portion 63, and provide mounting access to the corresponding carriage units 67.

Each saddle unit 70 includes a base portion 72 and a pair of opposed mounting flanges 73 that seat against and mount to a corresponding shoulder portion 75 in each access port 71 (FIG. 10), via fasteners. In turn, a substantially planar interior facing surface of each saddle unit 70 abuts against and is aligned with the substantially planar outer facing surface of the respective pair of carriage units 67. Using access cavities 76, the respective saddle unit 70 can be secured to the respective pair of carriage units 67, which in turn rigidly secure the carriage units to the actuation unit 33.

Accordingly, referring back to FIGS. 4 and 5, as the actuation unit 33 is rotated as a unit in a counterclockwise direction about the iris rotational axis 31, the wedge assembly 25 is also caused to rotate as a unit about the iris rotational axis 31 in the counterclockwise direction. Due to the intercoupling between the rotating actuation unit 33 and the stationary structure 32, the rotational motion is partially translated to linear motion of the slider mechanisms 36 as the respective carriage units 67 are caused to slide along their respective linear bearings 66. Consequently, the respective wedges 22 are then caused to rotate about their respective wedge rotational axis 34 at the respective pair of bearing devices 51. Simultaneously, the wedges are caused slide inwardly toward the crimp aperture 21 as the respective wheel flanges 55 of the bearing devices 51 navigate along the corresponding bearing slots 41 from an interior end to an exterior end thereof. Hence, the diameter of the crimp aperture 21 decreases in size from the opened aperture condition of FIGS. 1-4 to the closed aperture condition of FIG. 5. To move the wedges 22 outward to increase the size of the crimp aperture, the motion is simply reversed and will not be described in detail. Once the wedges reach the smallest crimp diameter, continuing past this point will cause the wedges to move back to the opened aperture condition. Minor adjustments, hence, would allow operation of this device in either direction (i.e., clockwise or counterclockwise.

In another embodiment of the present invention, it is further contemplated that the crimping system may additionally include a chiller unit (not shown) wherein the chiller unit is configured to chill or cool the chamber of the iris 30. This is advantageous when stents that must be cooled or chilled in order to reduce their diameters. For example, Nitinol stents must be cooled in order to reduce the diameter of the stent from an expanded diameter to a delivery diameter. The chiller may be integrally formed with the crimping system or may be a separate component that may be designed to work in conjunction with the apparatus.

Further still, it is contemplated that the end plates, drive plates or blades may be modified in order to function correctly with the chiller unit. The crimp aperture 21 itself, formed by the blades, is a highly insulated chamber, and is suitable for cryogenic processing. By providing an end cap 77 or the like, as illustrated in FIG. 10, the distal end of the crimp aperture 21 can be sufficiently sealed. As shown, the end cap 77 is formed for insertion into the receiving port 45 of the distal stationary end wall 35". A hub portion of the end cap is sized for a friction fit into the receiving port 45, and an O-ring 78 forms a fluid tight seal. A set of access ports 80, 81 extend through the end cap 77 that provide access to the crimp aperture 21 for selective cooling thereof.

Another embodiment includes cooling of the wedges themselves through cooling channels or passages. In this configuration, the blades could include communication orifices or the like that communicate a coolant from the coolant channels with the crimp aperture for cooling thereof.

Figure 12:
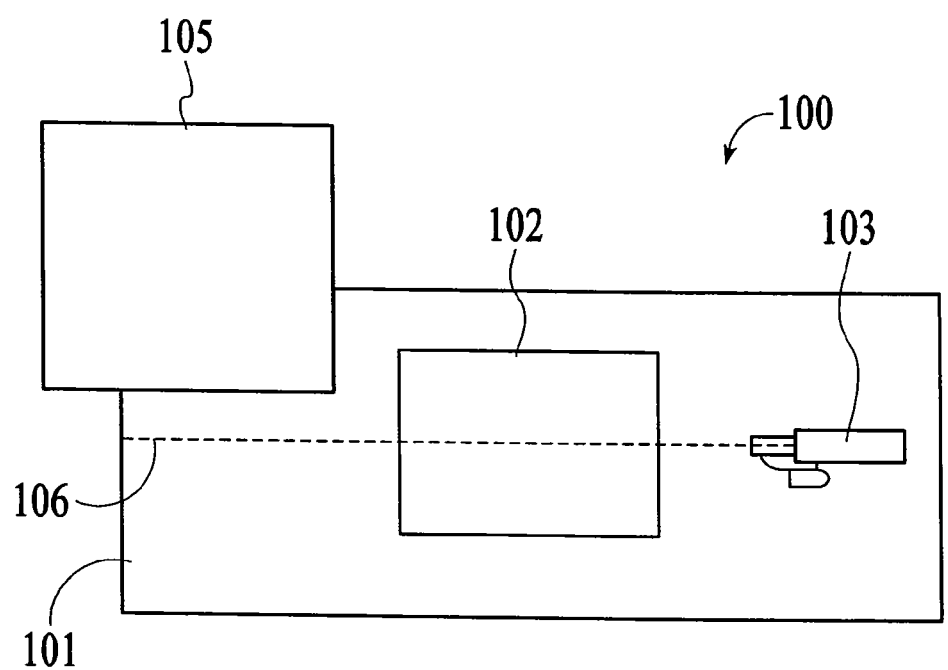
FIG. 12 is a top plan view of an alternative embodiment crimping system in accordance with the present invention.
Figure 13:
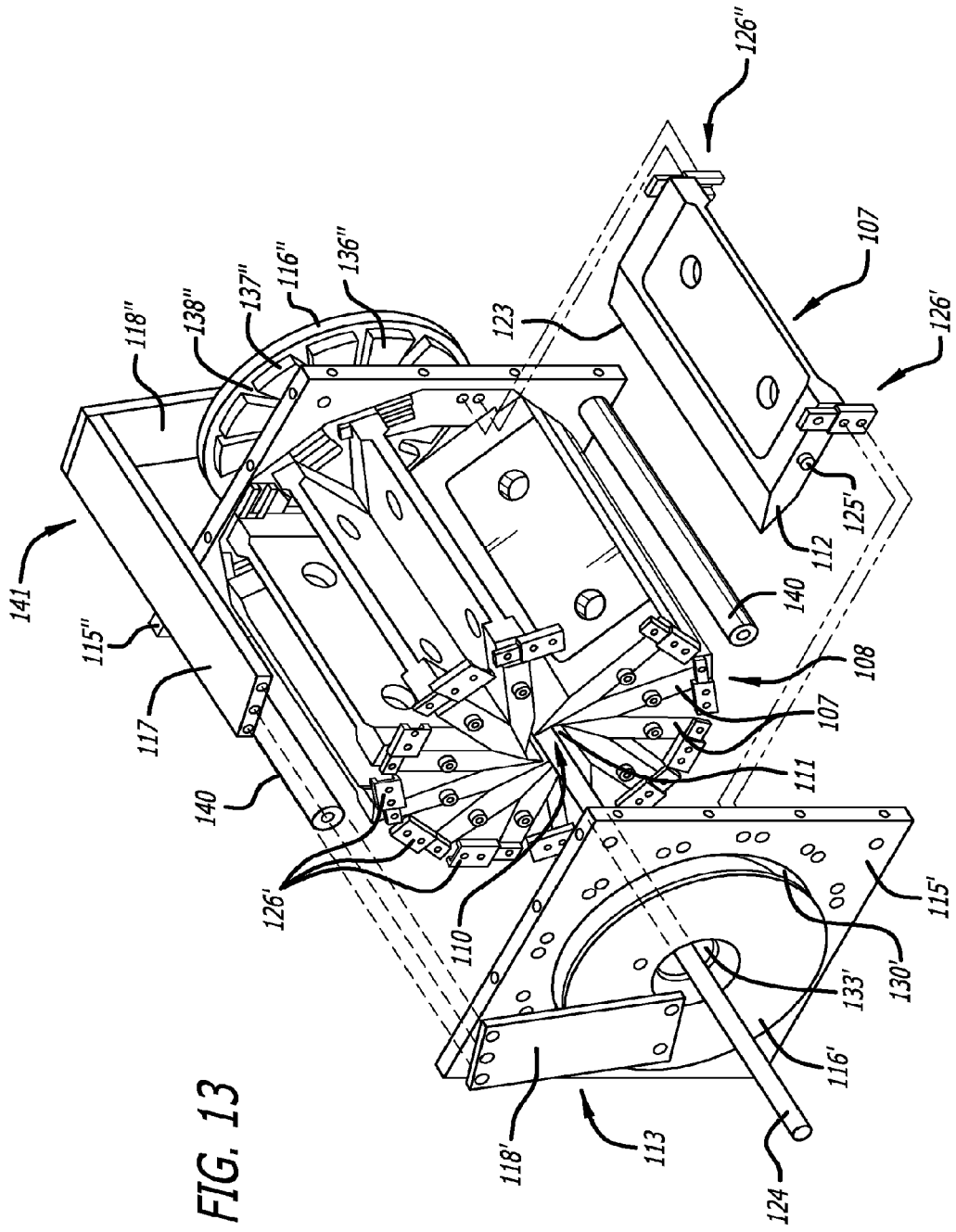
FIG. 13 is an exploded top perspective of an alternative embodiment crimp assembly of the crimping system of FIG. 12.
Figure 14:
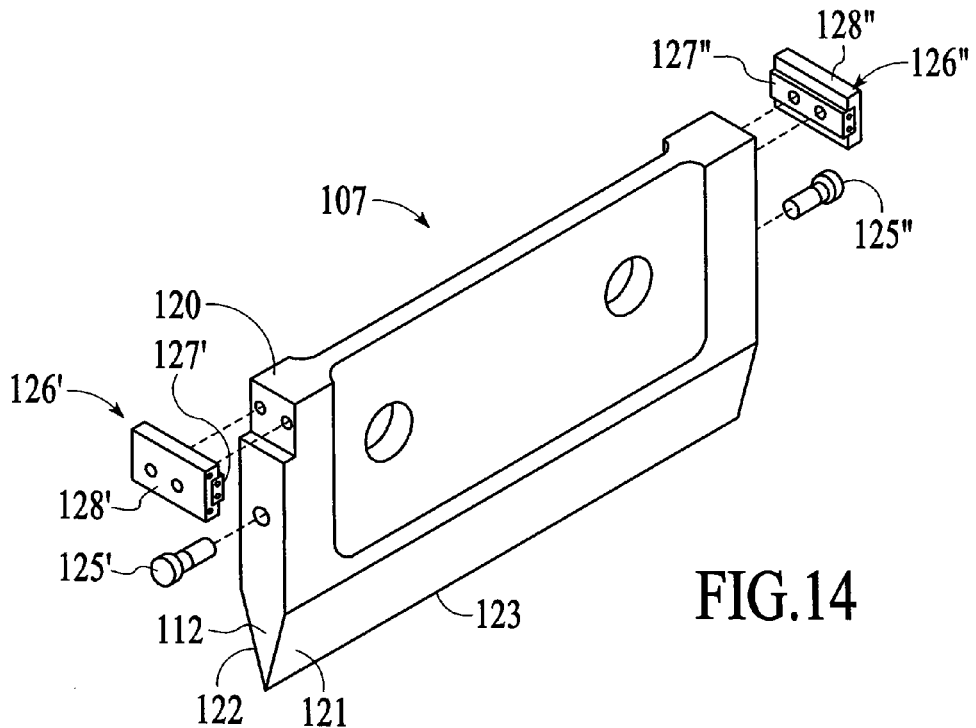
FIG. 14 is a top perspective view of a blade of the crimp assembly of FIG. 13.

Referring now to FIGS. 12-14, another aspect of the present invention is shown in which a stent crimping system, generally designated 100, includes a chassis or base member 101, a crimping assembly 102, a clamping assembly 103 and a control unit 105. The base member 101 is configured to retain the crimping assembly 102 and the clamping assembly 103 in alignment with one another, wherein the assemblies are aligned along a longitudinal axis 106. The base member further includes additional mechanical components (not shown) such as drive motors, load cells and other control mechanisms that are controlled by the control unit 105, wherein the control unit is programmed with a machine readable language to operate the mechanical components. In use, the control unit 105 may be associated with the control unit of the crimping assembly, wherein the control unit 105 would be utilized to control the expansion and contraction of the iris as described above. The control unit 105 may be user programmed to control the diameter of the iris within specified limits defined by the user. In the instances where a cryogenic cooler is utilized with the crimping assembly 102 it may be desirable to include a feedback loop within the control unit 105, wherein the feedback loop may be utilize to calibrate the diameter of the crimping assembly in combination with a quill of known diameter. In accordance with the present invention as shown in FIG. 13, there is provided a method of calibrating a crimping assembly in accordance with the present invention wherein the method includes the steps of (1) controlling a crimping assembly with a control unit, (2) calibrating the control unit with a quill 124 of known diameter by inserting the quill into the iris 110 and reducing the diameter of the iris onto the quill, (3) loading an endoprosthesis within an iris of the crimping assembly, (4) reducing the diameter of the iris to crimp the endoprosthesis, (5) loading the endoprosthesis into or onto a delivery system, and (6) calibrating the control unit. It is desirable to calibrate the control unit of the crimping assembly if a cryogenic cooler is being utilized during the crimping process due to tolerance changes of the iris as a result of contraction or expansion of the crimping assembly. By calibrating the diameter of the iris prior to crimping of the endoprosthesis a more consistent crimp diameter is achieved which is an improvement over conventional crimping techniques. It shall be understood that the process described above should be considered exemplary and not limiting in any manner. It is contemplated that the process may be modified, such as reducing or increasing the number of calibration cycles, utilizing a cooler before/during/or after the crimping process or other similar changes without departing from the scope of the invention.

The crimping assembly 102, as shown in FIG. 13, includes a plurality of wedges or blades 107 arranged in a wedge assembly 108 that forms an iris 110. At the center of the iris 110 is a crimp aperture 111 that is collectively formed by the distal end 112 of the blades 107. The crimping assembly 102 further includes a housing 113 having opposed end plates 115' and 115", opposed drive plates 116' and 116", a rotation arm 117, and rotator links 118' and 118". Disposed within the housing 113 is the wedge assembly containing the plurality of blades 107. Each blade 107 is associated with the opposed end plates 115', 115" and the drive plates 116', 116" of the housing.

These blades 107 of the wedge assembly 108 are configured to translate, whereby the diameter of the cylindrical crimp aperture 111 changes relative to the translation of the plurality of blades 107. The translation of the blades 107 may be performed manually by a user of the apparatus or, in a preferred embodiment, the crimping assembly 102 may be controlled by a control unit 105. The control unit, for instance, is provided by a computer or the like, wherein the computer includes a program designed to control the translation of the plurality of blades.

FIG. 14 best illustrates that blade 107 includes a proximal end 120 and the distal end 112, wherein a first side 121 and an opposed second side 122 adjacent to the distal end converge to form a tip 123. This tip 123 may be a sharp edge or may be slightly rounded or beveled as mentioned above. Each blade 107 may be constructed of a material or a combination of materials such as nylon, delrin, steel, aluminum, titanium, TEFLON @, plastics, composite materials, and other suitable materials. It is further contemplated that the blade 107 may be constructed of multiple pieces that may be assembled to form a unitary member, or alternatively blade 107 may be constructed as a unitary member.

It is further contemplated that blade 107 may further include a coating disposed thereon. For example, blade 107 may be coated with a coating that is configured to reduce friction, increase hardness, or alter other mechanical properties of the device according to the present invention. To reduce friction between adjacent blades or to reduce friction between the distal end portion of the blade and stent to be crimped, it is contemplated that the blade may be polished to a high degree in addition to or instead of coating the blade. For example, if it is desirable to form a blade of stainless steel, the blade may be constructed having a highly polished surface finish to reduce friction and to further reduce the possibility of scratching or otherwise damaging a stent to be crimped.

The blade 107 further includes a pair of opposed pivot pins 125', 125" disposed on each end section of the blade, wherein the pivot pins are aligned along an axis extending through a centerline plane of the blade and tip 123. In addition to the pivot pins 125', 125", the blade 107 further includes a pair of opposed sliding mechanisms 126', 126" disposed proximal to the respective pins 125', 125" and adjacent the proximal end 120 of the blade.

These sliding mechanisms 126', 126" comprises first members 127', 127" and second members 128', 128", wherein the respective first members 127', 127" are fixedly attached to the opposed ends of the blade 107 and the respective second members 128', 128" are slideably received by the corresponding first member 127', 127". As will be described in greater detail below with reference to additional drawing figures, the respective second members 128', 128" are configured to be fixedly attached to a corresponding end plate 115', 115" of the crimping assembly 100.

Figure 15:
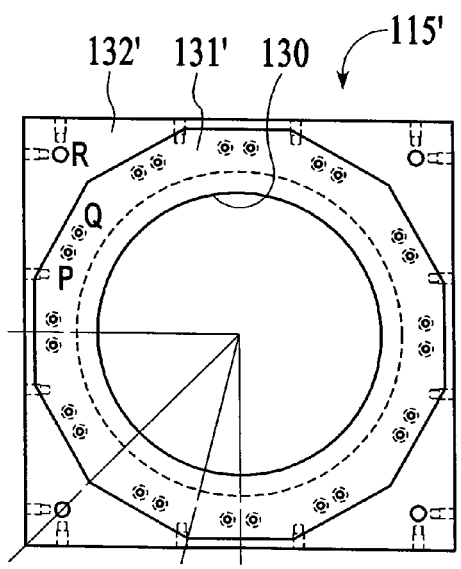
FIG. 15 is a front elevation view an end plate of the crimp assembly of FIG. 13.

Referring now to FIGS. 15 and 16 there is shown the end plates 115', 115" in accordance with the present invention, only end plate 115' of which will be described in detail. As shown, end plate 115' includes an aperture 130' extending therethrough from an outer surface to an inner surface. A recessed portion 131' surrounds the aperture 130', which in turn the respective second members 128' of the sliding mechanism 126' are fixedly supported. Each second member 128' of the sliding mechanism is fixedly attached to the end plate through suitable means, such as a fastener, welding or an appropriate adhesive. As shown, the inner surface 132' defines the recessed portion 131, sized of a depth similar to that of the depth of second member 128'. Hence, when the blades are slideably mounted to the opposed end plates 115', 115", the tolerance between the opposed ends of the blades 107 and that of the inner surfaces of the end plates 115', 115" is relatively small.

Figure 17A:
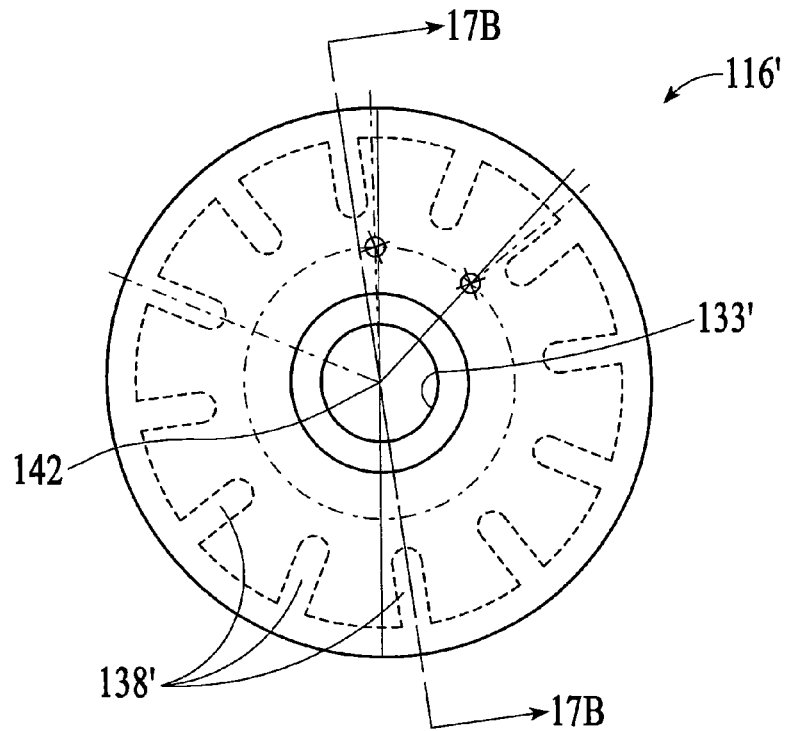
FIG. 17A is a front elevation view a drive plate of the crimp assembly of FIG. 13.
Figure 17B:
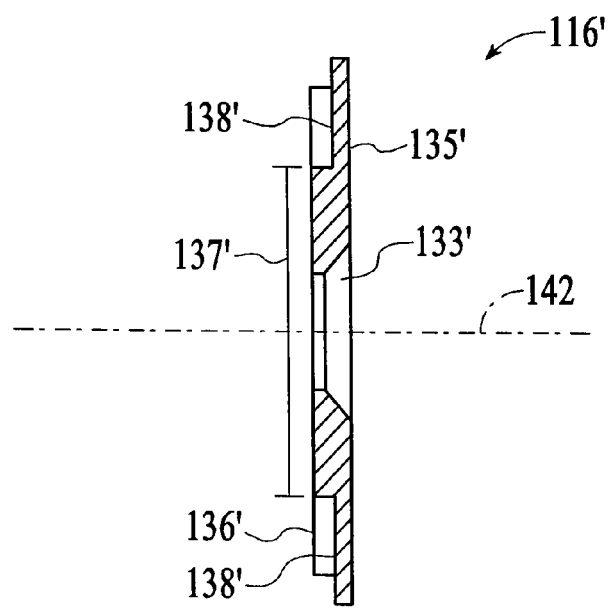
FIG. 17B is a side elevation view, in cross-section of the drive plate taken along the plane of the line 17B-17B in FIG. 17A.

Briefly, FIGS. 13, 17A and 17B illustrate that a respective drive plate 116', 116" is rotatably disposed into the respective aperture 133', 133" from the outer side of the respective end plate 115', 115". Only one drive plate 116' will be described in detail in which the aperture 133' is defined extending therethrough from first side 135' to a second side 136'. The second side 136' of the drive plate 116' further includes a hub portion 137' protruding from the surface thereof. The hub portion 137' is configured to be received within the aperture 130' of the corresponding end plate 115'. The hub portion 137' further includes a plurality of radially extending slots 138' that are disposed about the circumference of the hub. The slots 138' are configured to slideably receive the pivot pin 125' of the blades 107.

The end plates and the drive plates, as well as nearly all the components of the embodiments disclosed, may be constructed of materials such as metal, plastics or composites. In a preferred embodiment the end plates and the drive plates are constructed of rigid materials such as metal, such as steel or aluminum. The drive plates may be coated with a material to reduce friction between the drive plate and the end plate where the drive plate rotates within the aperture formed in the end plate.

Referring back to FIG. 13, there is shown an exemplary embodiment of the crimping assembly 102 in a partially exploded top perspective view. As illustrated, the crimping assembly 102 includes a housing 113 having two end plates 115', 115" coupled together by a two or more cross-beam 140. It will be appreciated, of course, that the blades 107 of the crimping assembly 102 could be enclosed entirely by enclosure structure as well, similar to the embodiment of FIGS. 1-11 above.

The crimping assembly further includes the two drive plates 116', 116" and an actuation device 141 comprising the laterally extending rotation arm 117 flanked by a pair of opposed rotator link 118', 118" fixedly mounted to the corresponding drive plates 116', 116". Disposed within the housing 113 is the wedge assembly 108 comprising the plurality of blades 107 such as those described in detail above. As assembled, each blade 107 is associated with each end plate 115', 115" at opposed sides thereof through the sliding mechanism 126', 126" and with each drive plate through the pivot pin 125', 125", for movement of the iris 110 from the first diameter to the reduced second diameter.

In accordance with the present invention, the crimping system shown and described herein may be utilized to reduce the diameter of a medical device (not shown) such as a stent from a first diameter to a second diameter. The stent may be comprised of either balloon expandable stents or self-expanding stents. The plurality of blades of the crimping assembly 102 are configured to be movable, wherein the distal portions of the blades and the blade tips form an iris 110 having the crimp aperture 111. The aperture may be moved between a first diameter and a second diameter, wherein the first diameter is of sufficient size to receive an expanded or uncrimped stent. After placing the sent within the crimp aperture 111 of the iris 110, a force is applied to either the rotation arm 117 or rotator links 118', 118", thereby rotating the drive plate 116', 116". During rotation of the drive plates 116', 116" about the rotational axis 142, the interior walls defining the radial slots 138', 138" of the second side 136', 136", cause the blade tips 123 to pivot about the pivot pins 125', 125", while linearly translating in the direction of the respective slider mechanism 126', 126". This combination of motion causes closure of the blade tips 123 (and hence the crimp aperture 111 of the iris 110) from the first diameter to the second diameter. Accordingly, the rotation of the drive plates are translated to the plurality of blades which are in communication with the drive plates, via the opposed slider mechanism 126', 126" and pivot pins 125', 125".

The rotation arm or rotator links can be rotated manually by a user or automatically through the control system of the present invention. If the stent is a balloon expandable stent, prior to applying a force to the blades, a delivery system such as a balloon catheter is disposed within the crimp aperture, whereby as the aperture is drawn closed the stent is crimped about the balloon of the delivery device.

In another aspect of the present invention, the clamping assembly 103 is shown and described in detail in reference to FIGS. 18-21. This clamping assembly 103 is particularly suitable for securing a medical device, such as a delivery catheter for pre-operative preparation applications. For example, as shown in the schematic diagram of FIG. 12, a delivery catheter (not shown) may be secured by the clamp assembly 103 while it's delivery portion is aligned along the longitudinal axis 106 and disposed in the crimper assembly 102 so that a crimp procedure can be performed.

Briefly, the clamping assembly 103 includes a lower clamp device 145, an upper clamp device 146, two opposed pivot levers 147', 147", a catheter retaining assembly 148, and a clamp actuation mechanism 150. As will be detailed below, these components cooperate to move the retaining assembly 148 between an opened condition (FIGS. 19, 21, 24 and 26), enabling insertion and positioning of the delivery device therein, and a closed condition (FIGS. 20, 22, 25 and 27), clamping the delivery device in place.

Figure 18:
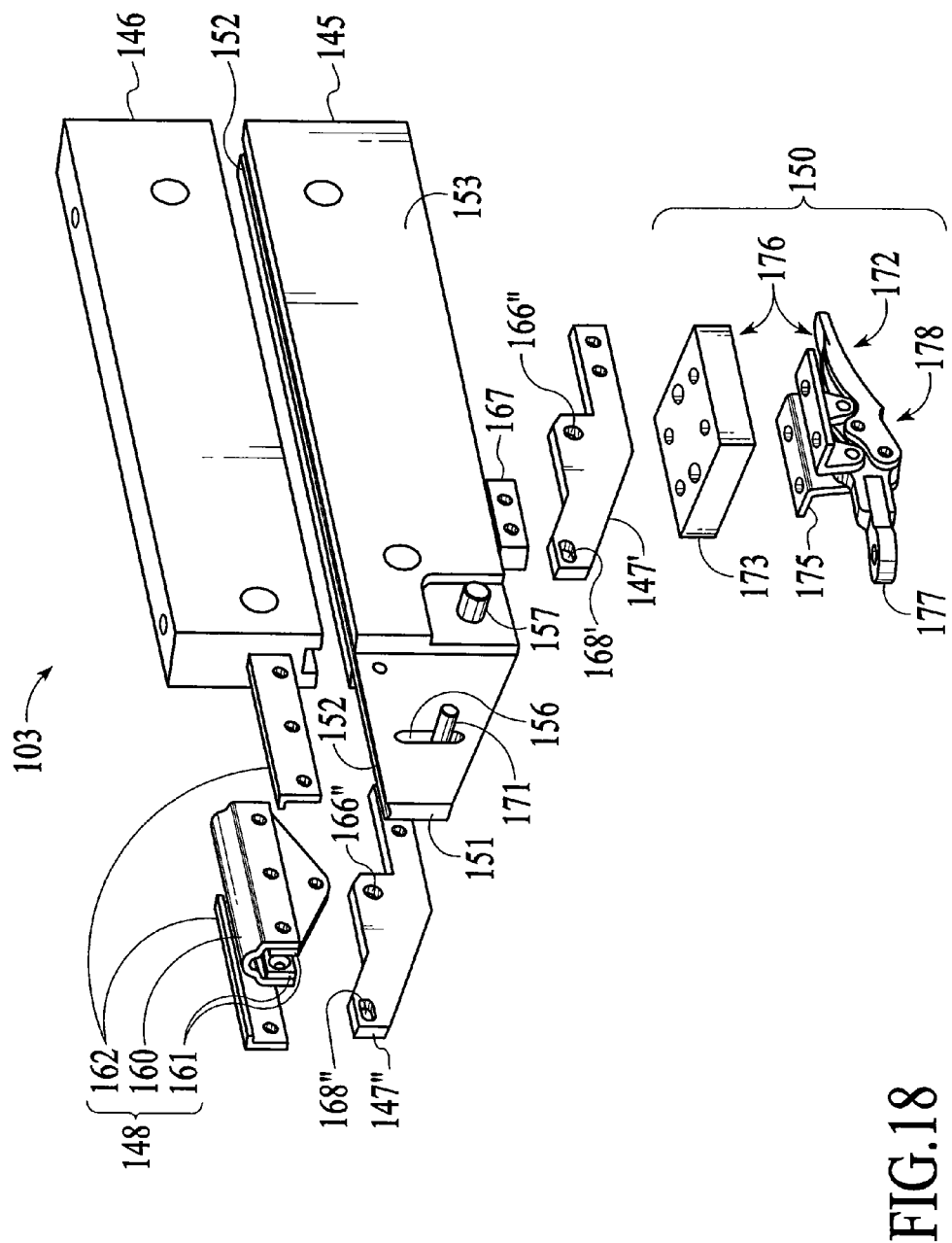
FIG. 18 is an exploded top perspective view of a clamping assembly constructed in accordance with of the present invention.
Figure 19:
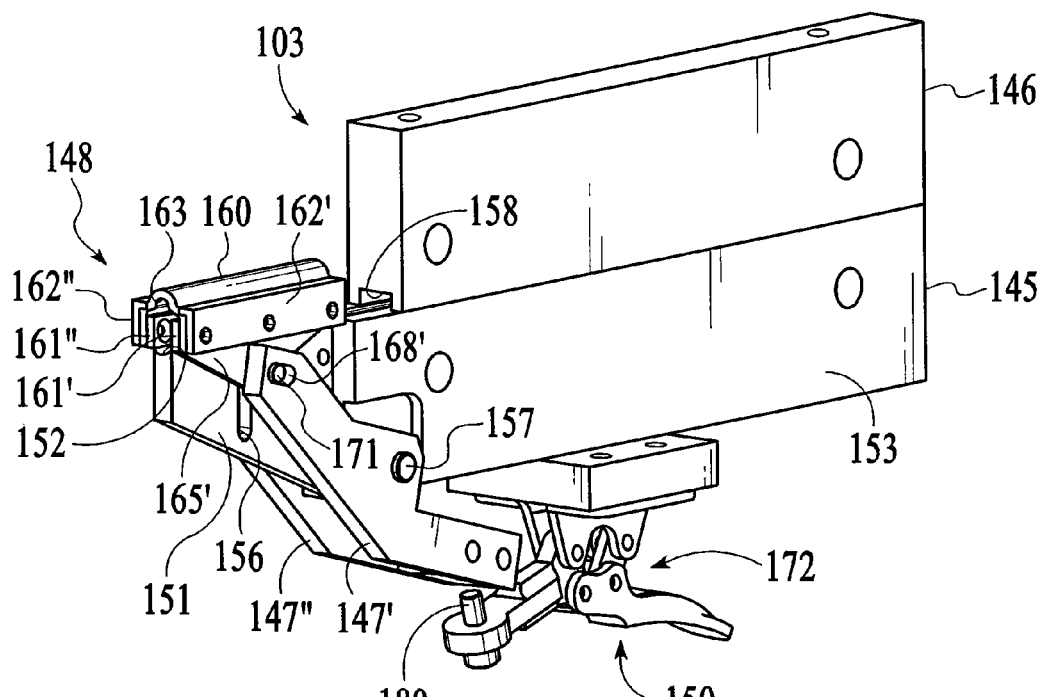
FIG. 19 is a top perspective view of the clamping assembly of FIG. 18, illustrated in an opened condition.
Figure 20:
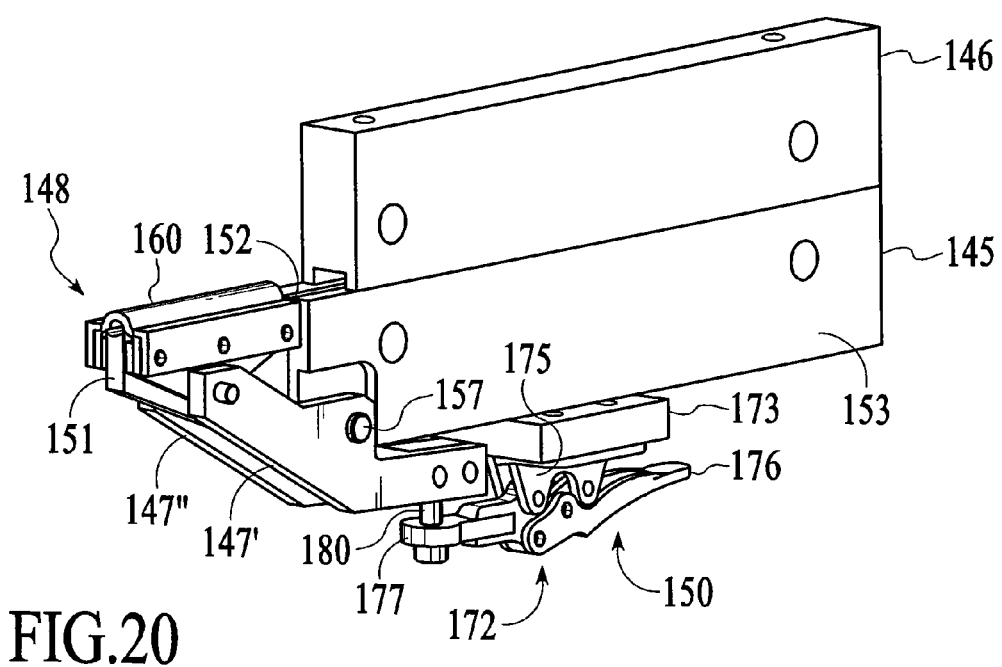
FIG. 20 is a top perspective view of the clamping assembly of FIG. 20, illustrated in a closed condition.
Figure 21:
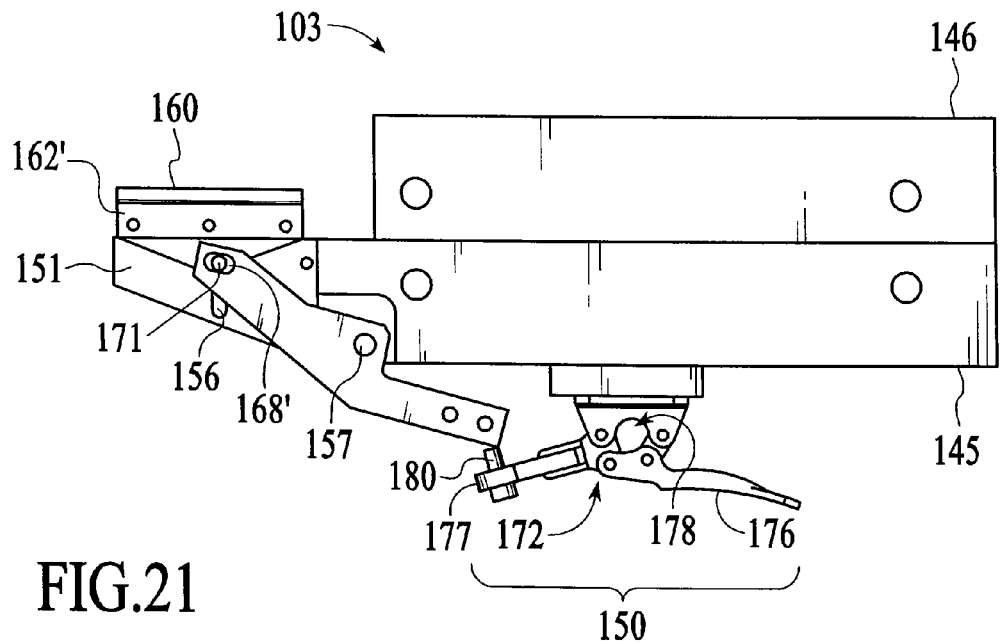
FIG. 21 is a side elevation view of the clamping assembly of FIG. 19, illustrated in the opened condition.
Figure 22:
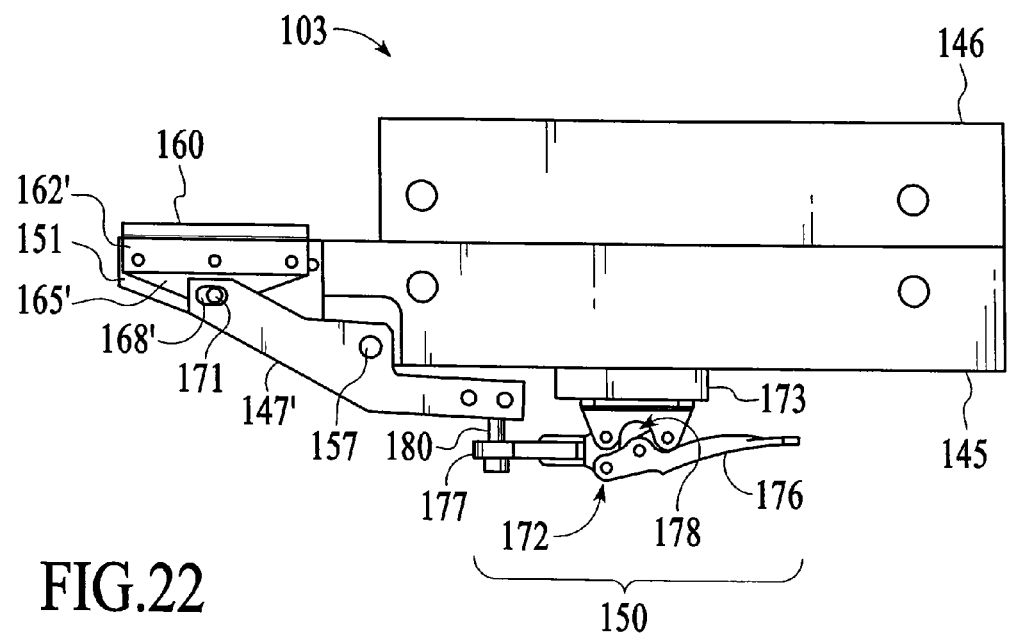
FIG. 22 is a side elevation view of the clamping assembly of FIG. 21, illustrated in the closed condition.

The lower clamp device 145 includes an elongated base 153 with a support plate 151 extending distally therefrom. The base 153 and the support plate 151 define a half-round or semi-circular-shaped seating groove 152 extending along an upper edge thereof (FIGS. 18, 20 and 26). This groove 152 is configured to receive a specific sized delivery device. In the event that other delivery devices are to be utilized with the clamp assembly 103, the groove 152 should be sized accordingly. It will be appreciated that the groove 152 need not be perfectly semi-circular. For example, it may be semi-polygonal shaped as well. The diameter or width of the groove 152, however, should be at least the same as the outer diameter of the delivery device.

The elongated support plate 151 includes an elongated slot 156 that is oriented vertically. As will be described below, this elongated slot accommodates a securing pin 171 that mounts the pivot levers 147', 147" to the retaining assembly 148, during movement of between the opened condition and the closed condition. The lower clamp further includes a pair of opposed pivot pins 157 extending outwardly in a direction substantially perpendicular to the elongated support plate.

Figure 23:
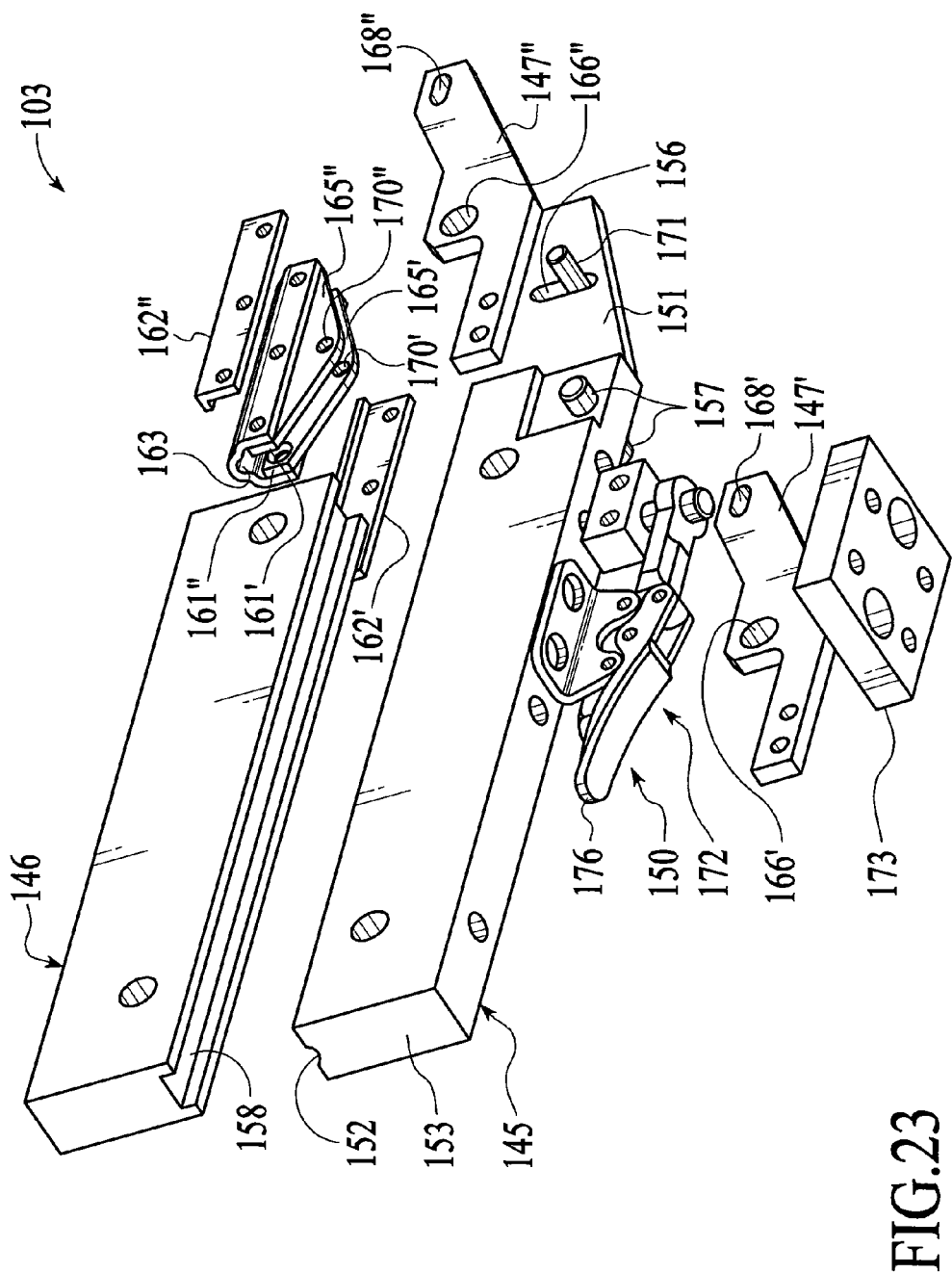
FIG. 23 is an exploded bottom perspective view of the clamping assembly of FIG. 18.

The upper clamp device 146 is utilized to mount the clamp assembly 103 to the base 101, and in alignment with the crimping assembly 102 (FIG. 12). It shall be understood, however, that the upper clamp device 146 may not be required in order for the clamp assembly to function as desired. As best shown in FIGS. 20 and 23, the upper clamp device 146 also includes an elongated base having a rectangular shaped channel 158 extending along a lower edge portion thereof. The upper clamp device channel 158 is significantly wider than the seating groove 152 of the lower clamp device 145. When the upper clamp device 146 is mounted to the lower clamp device 145, a collective receiving channel is formed (FIGS. 24 and 25) that can accommodate the entire transverse cross-sectional dimension of the delivery device therethrough.

The catheter retaining assembly 148 includes an elongated U-shaped elastomeric member 160, a pair of spaced-apart inner plates 161', 161" and a pair of spaced-apart outer plates 162', 162". The U-shaped elastomeric member is inverted such that an elongated contacting groove 163 thereof faces downwardly, in opposed relation to the elongated seating groove 152 of the lower clamp device support plate 151. Each downwardly depending side wall of the elastomeric member 160 is straddled by a respective inner plate 161', 161" and a respective outer plate 162', 162". These plates are secured together with the appropriate fasteners (e.g., screws, bolts, rivets or similar attachment devices and methods), and provide structural support to the elastomeric member 160.

When the retaining assembly 148 is moved to the closed condition (FIGS. 20, 22, 25 and 27), the elongated contacting groove 163 thereof contacts an upper side of the delivery device, and urges it securely against seating groove 152 of the support plate 151. Hence, the elastomeric member 160 is preferably composed of an elastic material that provides sufficient elasticity to secure the delivery device without threatening the integrity of the delivery device components or materials. By way of example, the elastomeric member 160 may be composed of silicon rubber, rubber, latex, PVC or similar materials.

The two inner plates 152 include a downwardly depending vertical wing portion 165', 165", each of which is employed to cooperate with the pivot levers 147', 147" for movement thereof between the opened and closed conditions. As best illustrated in FIGS. 19, 20, 24 and 25, the pivot levers 147', 147" include pivot apertures 166', 166" formed to receive the pivot pins 157 of the lower clamp device. A proximal end of the pivot levers 147', 147" includes a contact block 167 disposed between the two levers for structural integrity thereof. At a distal end of each pivot lever 147', 147" is a pin receiving slot 168', 168", each of which is configured for co axial alignment with a pin receiving port 170', 170" in the inner plate wing portions 165', 165". When the pin receiving slot 168', 168" and 170', 170" are co-axially aligned with the vertical slot 156 of the elongated support plate 151, a securing pin 171 is passed therethrough to mount these components together. Accordingly, as the pivot levers 147', 147" are caused to rotate about a rotational axis 174 (FIGS. 26 and 27) of the pivot pins 157, the retaining assembly, via the distal end of the pivot levers 147', 147" and the securing pin 171, is caused to move between the opened condition (FIGS. 19, 21, 24 and 26) and the closed condition (FIGS. 20, 22, 25 and 27).

The lever pin receive slot 168', 168" are horizontally or laterally elongated while the support plate elongated slot 156 is vertically elongated. In either case, these slots are configured to accommodate the travel of the securing pin 171 during reciprocal movement of the retaining assembly between the opened condition and the closed condition.

Figure 24:
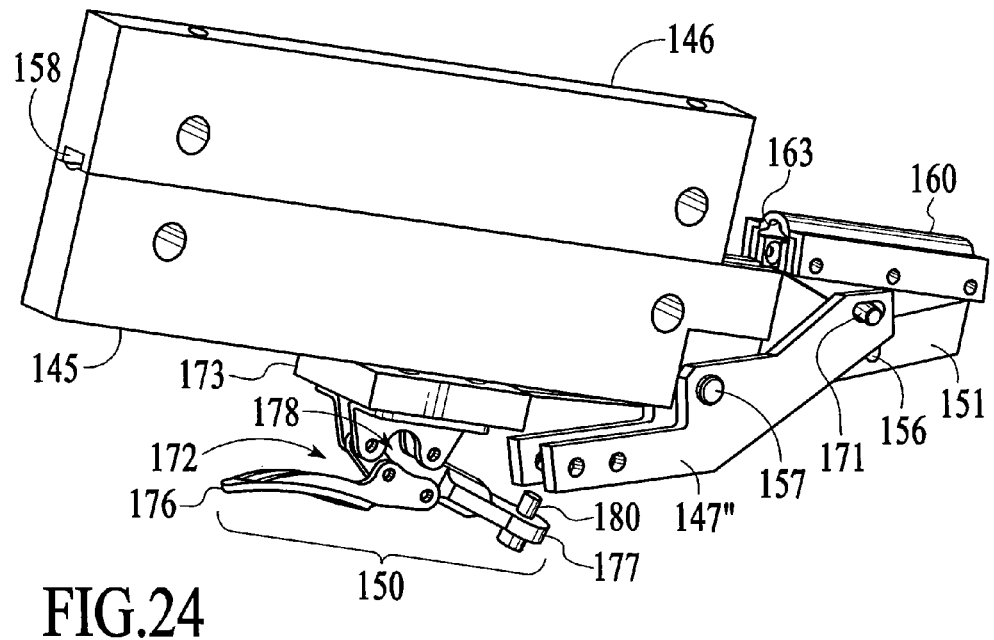
FIG. 24 is a bottom perspective view of the clamping assembly of FIG. 23, illustrated in the opened condition.
Figure 25:
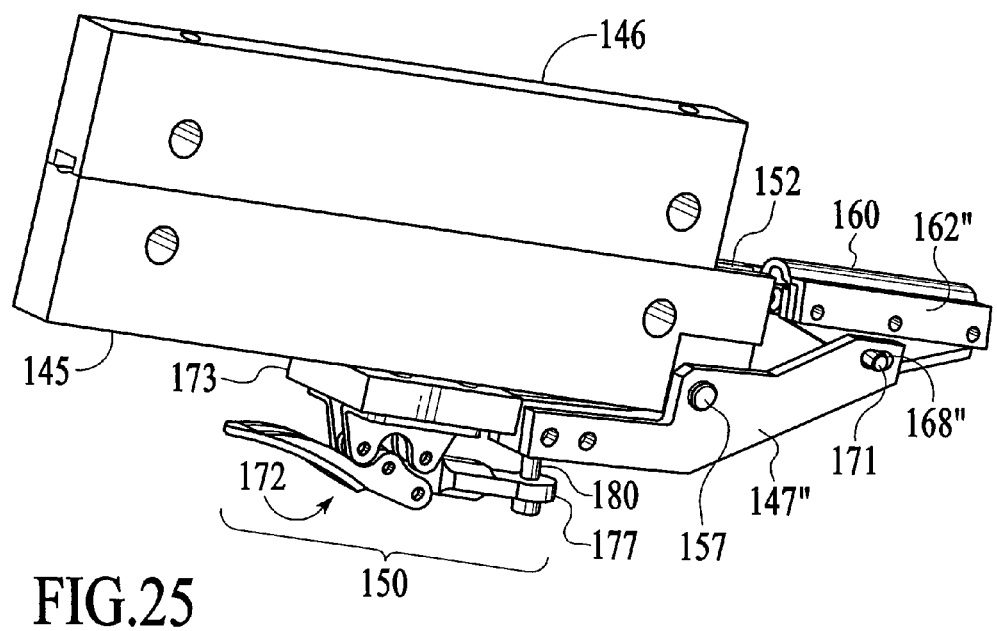
FIG. 25 is a bottom perspective view of the clamping assembly of FIG. 23, illustrated in the closed condition.

Briefly, the movement of the pivot levers 147', 147" is controlled through the clamp actuation mechanism 150 that is configured to contact the contact block 167 at the proximal end thereof. As best illustrated in FIGS. 23-25, the actuation mechanism 150 includes a clamp bracket 172 and a support base 173 that is configured to mount the clamp bracket to the lower clamp device 145. The clamp bracket 172 includes a bracket base 175, a lever member 176, a contact lever 177 and a four-bar linkage assembly 178 that cooperates to move the contact lever 177 between a first position (FIG. 24) and a second position (FIG. 25). In the second position, contact lever 177 contacts the contact block 167, and rotates the pivot levers about the pivot pin rotational axis 174.

The contact lever 177 can include a threaded contact screw 180 or the like that can be adjusted to adjust the contact against the contact block. While this one clamp actuation mechanism embodiment is shown and described, it will be appreciated that other conventional mechanism can be employed as well.

In operation, when the clamping assembly 103 is in the opened condition (FIGS. 19, 21, 24 and 26), the lever member 176 of the clamp actuation mechanism 150 is manually operated to move the contact lever 177 from the first position (FIG. 24) to the second position (FIG. 25), via the linkage assembly 178. In the second condition, the contact lever 177 moves the contact screw 180 against the contact block 167 with a force sufficient to urge the proximal end of the pivot levers 147', 147" about the pivot pins 157. As the pivot lever 147', 147" rotates about the rotational axis 174 of the pivot pins 157, the distal end of the levers urge the catheter retaining assembly 148, via the securing pin 171, toward the closed position (FIGS. 20, 22, 25 and 27). Accordingly, the downward force of the elastomeric member 160 of the catheter retaining assembly thereby retains the catheter or delivery device between the retaining assembly and the seating groove 152 at the support plate 151.

In addition to that described above, an important functionality of this clamp assembly is its ability to hold and retain a stent delivery device with sufficient force to prevent the device from moving relative to the clamp but with not too large a force where the delivery device is damaged. The force applied to the delivery device may be adjusted by adjusting the properties of the elastomeric material or by adjusting the clamping force applied to the elastomeric material by the clamping assembly.

As set forth above with crimping assembly of FIGS. 1-11, it is further contemplated that the crimping system 100 in accordance with the present invention may additionally include a chiller unit (not shown) wherein the chiller unit is configured to chill or cool the crimping assembly 102 such that the crimping assembly 102 may then be utilized with stents that must be cooled or chilled in order to reduce their diameters. For example, Nitinol stents must be cooled in order to reduce the diameter of the stent from an expanded diameter to a delivery diameter. The chiller may be integrally formed with the crimping system 100 or may be a separate component that may be designed to work in conjunction with the apparatus. Further still, it is contemplated that the end plates, drive plates or blades may be modified in order to function correctly with the chiller unit.

If the stent to be crimped is a self-expanding stent, prior to applying a force to the blades, a delivery device is disposed within the clamp assembly. Once the stent has been crimped to a desirable delivery diameter, the clamp assembly is advanced toward the crimping assembly, or alternatively, the crimping assembly is advanced toward the clamp assembly, wherein the crimped stent is then disposed within the delivery device and the opening is enlarged by either removing the applied force or applying a force opposite of that previously applied.

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed:

1. A method of calibrating a crimping assembly, comprising:
controlling a crimping assembly with a control unit;
calibrating the control unit by inserting a quill of a known diameter into an iris of the crimping assembly and reducing a diameter of the iris onto the quill;
loading an endoprosthesis within the iris of the crimping assembly; and
reducing the diameter of the iris to crimp the endoprosthesis.

2. The method of claim 1, wherein the control unit is operably coupled to a drive mechanism and programmed to operate the drive mechanism to control an expansion and a contraction of the iris.

3. The method of claim 1, wherein the crimping assembly comprises:
a pair of spaced end plates;
a pair of spaced drive plates, each rotatably associated with one of the end plates about a rotational axis thereof;
a plurality of blades disposed between the drive plates and disposed about the rotational axis;
each blade having a first end section and an opposed second end section, each end section being pivotally coupled to the respective drive plates;
each blade having a proximal edge and a distal edge, and a tapered portion adjacent to the distal edge, the distal edge being parallel to the rotational axis, wherein a first side and a second side of the tapered portion of each blade is arranged substantially adjacent a second side and a first side, respectively, of the tapered portion of an adjacent blade such that the distal edge portions collectively form an iris, said iris defining a crimp aperture.

4. The method of claim 1, further comprising:
cooling the crimping assembly with a cryogenic cooler; and
calibrating the control unit during the crimping process to adjust for a tolerance change of the iris as a result of a contraction or an expansion of the iris.

5. The method of claim 1, wherein the control unit is programmed with machine readable language for sending instructions to a drive motor.

6. The method of claim 1, wherein the control unit is programmable to control the diameter of the iris within specified limits.

7. The method of claim 1, wherein the control unit includes a feedback control loop for calibrating the diameter of the iris using the quill of a known diameter.

8. A method of calibrating a crimping assembly, comprising:
controlling a crimping assembly with a control unit;
calibrating the control unit by inserting a quill of a known diameter into an iris of the crimping assembly and reducing a diameter of the iris onto the quill;
loading an endoprosthesis within the iris of the crimping assembly;
reducing the diameter of the iris to crimp the endoprosthesis;
loading the endoprosthesis into or onto a delivery system; and
calibrating the control unit.

9. The method of claim 8, wherein the control unit is operably coupled to a drive mechanism and programmed to operate the drive mechanism to control an expansion and a contraction of the iris.

10. The method of claim 8, wherein the crimping assembly comprises:
a pair of spaced end plates;
a pair of spaced drive plates, each rotatably associated with one of the end plates about a rotational axis thereof;
a plurality of blades disposed between the drive plates and disposed about the rotational axis;
each blade having a first end section and an opposed second end section, each end section being pivotally coupled to the respective drive plates;
each blade having a proximal edge and a distal edge, and a tapered portion adjacent to the distal edge, the distal edge being parallel to the rotational axis, wherein a first side and a second side of the tapered portion of each blade is arranged substantially adjacent a second side and a first side, respectively, of the tapered portion of an adjacent blade such that the distal edge portions collectively form an iris, said iris defining a crimp aperture;
the control unit sending instructions to a drive motor for rotating the drive plates about the rotational axis causing the distal edge of the plurality of blades to pivot while linearly translating along respective slider assemblies for movement of the iris from a first diameter to a second diameter.

11. The method of claim 8, further comprising:
cooling the crimping assembly with a cryogenic cooler; and
calibrating the control unit during the crimping process to adjust for a tolerance change of the iris as a result of a contraction or expansion of the crimping assembly.

* * * * *